US012802780B2

(12) United States Patent
Muerdter et al.

(10) Patent No.: US 12,802,780 B2
(45) Date of Patent: Nov. 17, 2026

(54) METHODS AND SYSTEMS FOR SEQUENCE GENERATION AND PREDICTION

(71) Applicant: REGENERON PHARMACEUTICALS, INC., Tarrytown, NY (US)

(72) Inventors: Felix Muerdter, Tarrytown, NY (US); Christopher Schoenherr, Tarrytown, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 886 days.

(21) Appl. No.: 18/171,045

(22) Filed: Feb. 17, 2023

(65) Prior Publication Data

US 2023/0298698 A1 Sep. 21, 2023

Related U.S. Application Data

(63) Continuation of application No. PCT/US2021/046975, filed on Aug. 20, 2021.

(60) Provisional application No. 63/068,654, filed on Aug. 21, 2020.

(51) Int. Cl.

| | |
|---|---|
| ***G16B 25/10*** | (2019.01) |
| ***G16B 5/20*** | (2019.01) |
| ***G16B 40/20*** | (2019.01) |

(52) U.S. Cl.
CPC ............... *G16B 25/10* (2019.02); *G16B 5/20* (2019.02); *G16B 40/20* (2019.02)

(58) Field of Classification Search
None
See application file for complete search history.

(56) References Cited

U.S. PATENT DOCUMENTS

2019/0073443 A1 3/2019 Frey et al.

FOREIGN PATENT DOCUMENTS

| | | | |
|---|---|---|---|
| AU | 2021327765 | 8/2021 | |
| CA | 3190092 | 8/2021 | |
| CN | 2021800706573 | 8/2021 | |
| EP | 21859228.5 | 8/2021 | |
| HK | 62023084020.4 | 12/2023 | |
| JP | 223-512747 | 8/2021 | |
| JP | 2023-512747 | 8/2021 | |
| SG | 10202302348 | 8/2021 | |
| SG | 11202301272 | 8/2021 | |
| WO | 1999/066302 A2 | 12/1999 | |
| WO | 2007078599 A2 | 7/2007 | |
| WO | WO-2018064208 A1 * | 4/2018 | ............. G16H 50/30 |
| WO | PCT/US2021/046975 | 8/2021 | |

OTHER PUBLICATIONS

Linder et al. ("A Generative Neural Network for Maximizing Fitness and Diversity of Synthetic DNA and Protein Sequences", Cell Systems, vol. 11, Issue 1, published Jul. 22, 2020. (Year: 2020).*
Zhao et al. ("Systematic clustering of transcription start site landscapes". PLoS One, 6(8), published Aug. 24, 2011. (Year: 2011).*
U.S. Appl. No. 63/068,654, filed Aug. 21, 2020, Felix Muerdter.
Oubounyt et al., "DeePromoter: Robust PromoterPredictor Using DeepLearning", 2019, Frontiers in Genetics, vol. 10, No. 286, https://doi.org/10.3389/fgene.2019.00286 (9 pages).
Wang et al., "Synthetic Promoter Design in *Escherichia coli* based on Generative Adversarial Network", 20190, bioRxiv, https://doi.org/10.1101/563775, 10 pages.
Abeel, T. et al., "ProSom: core promoter prediction based on unsupervised clustering of DNA physical profiles," Bioinformatics 24(13):i24-i31 (2008).
Fuchs, et al., "A general method for rapid and cost-efficient large-scale production of 5' capped RNA," RNA, Sep. 2016;22(9): 22:1454-66.
Georgakilas, GK et al., "Solving the transcription start site identification problem with ADAPT-CAGE: a Machine Learning algorithm for the analysis of CAG date," 10(1): Article 877, pp. 1-12 (2020).
Kelley, DR, "Cross-species regulatory sequence activity prediction," PLOS Computational Biology 16(7): Article e1008050, pp. 1-27 (2020).
Zabidi, et al., "Regulatory Enhancer-Core-Promoter Communication via Transcription Factors and Cofactors," Trends Genet. Dec. 2016;32(12):801-814.
International Search Report and Written Opinion mailed Feb. 7, 2022 in PCT/US2021/46975 (16 Pages).
Im et al., "A generative model for constructing nucleic acid sequences binding to a protein", BMC Genomics, vol. 20, No. S13, 2019, http://link.springer.com/article/10.1186/s12864-019-6299-4/fulltext.html (13 pages).

* cited by examiner

*Primary Examiner* — Heather Calamita
*Assistant Examiner* — Jessica D Parisi
(74) *Attorney, Agent, or Firm* — Ballard Spahr LLP

(57) ABSTRACT

A computational framework for generating and predicting regulatory sequences is described.

20 Claims, 23 Drawing Sheets

Specification includes a Sequence Listing.

1800

METHODS AND SYSTEMS FOR SEQUENCE GENERATION AND PREDICTION

CROSS REFERENCE TO RELATED APPLICATIONS

This application is a continuation of PCT Application No. PCT/US2021/046975, filed Aug. 20, 2021, which claims the benefit of priority of the filing date of U.S. Provisional Application No. 63/068,654, filed on Aug. 21, 2020. The content of these earlier filed application is hereby incorporated by reference in their entirety.

REFERENCE TO SEQUENCE LISTING

The Sequence Listing submitted Feb. 17, 2023 as a xml file named "37595_0033U2.xml," created on Feb. 17, 2023, and having a size of 13,555 bytes is hereby incorporated by reference pursuant to 37 C.F.R. § 1.52(e)(5).

BACKGROUND

Adeno-associated viruses (AAV) are the gold standard for delivery of transgenes in gene therapy. While offering many advantages such as low immunogenicity and strong infectivity, one limitation is its strict DNA packaging capacity. Many therapeutic modalities already approach this limit. Together with other features encoded in recombinant AAV vectors this leaves little space for regulatory sequences. Both commonly used viral and endogenous mammalian promoters exceed these limitations and cannot be used for AAV-mediated delivery of large transgenes. Thus, there is a strong need for short and efficient regulatory sequences.

BRIEF SUMMARY

Disclosed are methods comprising receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the associated expression scores satisfying a threshold, a plurality of TSSs from the first plurality of nucleotide sequences, determining, based on the plurality of TSSs, a plurality of summit nucleotide bases, determining, for each summit nucleotide base of the plurality of summit nucleotide bases, an associated plurality of surrounding bases, storing each summit nucleotide base and the associated plurality of surrounding bases as a second plurality of nucleotide sequences labeled as core promoters, determining, for each nucleotide sequence of the second plurality of nucleotide sequences, an associated plurality of shifted bases, storing each associated plurality of shifted bases as a third plurality of nucleotide sequences labeled as not core promoters, generating, based on the second plurality of nucleotide sequences labeled as core promoters and the third plurality of nucleotide sequences labeled as not core promoters, a training data set, determining, based on the training data set, a plurality of features for a predictive model, training, based on a first portion of the training data set, the predictive model according to the plurality of features, testing, based on a second portion of the training data set, the predictive model, and outputting, based on the testing, the predictive model.

Also disclosed are methods comprising receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the second plurality of nucleotide sequences, a third plurality of nucleotide sequences labeled as not core promoters, generating, based on the second plurality of nucleotide sequences labeled as core promoters and the third plurality of nucleotide sequences labeled as not core promoters, a training data set, determining, based on the training data set, a plurality of features for a predictive model, training, based on a first portion of the training data set, the predictive model according to the plurality of features, testing, based on a second portion of the training data set, the predictive model, and outputting, based on the testing, the predictive model.

Also disclosed are methods comprising receiving genetic data, wherein the genetic data comprises a first plurality of nucleotide sequences, wherein each nucleotide sequence of the plurality of nucleotide sequences comprises at least one transcription start site (TSS) having an associated expression score, normalizing the genetic data, clustering, based on the associated expression scores, the TSSs, determining, for each cluster of TSSs, an interquantile width, labeling, based on the interquantile width, each TSS as a sharp TSS or a broad TSS, determining, based on the plurality of TSSs, a plurality of summit nucleotide bases, determining, for each summit nucleotide base of the plurality of summit nucleotide bases, an associated plurality of surrounding bases, storing each summit nucleotide base and the associated plurality of surrounding bases as a second plurality of nucleotide sequences labeled as core promoters, determining, based on the associated expression scores satisfying a threshold, a third plurality of nucleotide sequences from the second plurality of nucleotide sequences, determining, for each nucleotide sequence of the third plurality of nucleotide sequences, an associated plurality of shifted bases, storing each associated plurality of shifted bases as a fourth plurality of nucleotide sequences labeled as not core promoters, generating, based on the third plurality of nucleotide sequences labeled as core promoters and the fourth plurality of nucleotide sequences labeled as not core promoters, a training data set, generating, for each nucleotide sequence in the training data set, a plurality of seed sequence and target nucleotide pairs, vectorizing each seed sequence and target nucleotide pair of the plurality of seed sequence and target nucleotide pairs, training, based on the vectorized seed sequence and target nucleotide pairs, a generative model, and outputting the generative model.

Also disclosed are methods comprising receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the associated expression scores satisfying a threshold, a third plurality of nucleotide sequences from the second plurality of nucleotide sequences, determining, based on the third plurality of nucleotide sequences, a fourth plurality of nucleotide sequences labeled as not core promoters, generating, based on the third plurality of nucleotide sequences labeled as core promoters and the fourth plurality of nucleotide sequences labeled as not core promoters, a training data set, training, based on the training data set, a generative model, and outputting the generative model.

Also disclosed are methods comprising receiving a nucleotide sequence, providing, to a trained predictive model, the nucleotide sequence, and determining, based on the predictive model, that the nucleotide sequence is a core promoter.

Also disclosed are methods comprising: (a) receiving a nucleotide sequence and a sequence length, (b) providing, to a trained generative model, the nucleotide sequence, (c) determining, based on the generative model, a next nucleotide associated with the nucleotide sequence, (d) appending the next nucleotide to the nucleotide sequence, (e) repeating b-d until a length of the nucleotide sequence equals the sequence length, and (f) outputting the nucleotide sequence as a core promoter sequence.

Also disclosed are methods comprising receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the associated expression scores satisfying a threshold, a third plurality of nucleotide sequences from the second plurality of nucleotide sequences, determining, based on the third plurality of nucleotide sequences, a fourth plurality of nucleotide sequences labeled as not core promoters, generating, based on the third plurality of nucleotide sequences labeled as core promoters and the fourth plurality of nucleotide sequences labeled as not core promoters, a training data set, training, based on the training data set, a generative model.

Disclosed are apparatuses configured to perform any of the disclosed methods.

Disclosed are computer readable mediums having processor-executable instructions embodiment thereon configured to cause an apparatus to perform any of the disclosed methods.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a p art of this specification, illustrate several embodiments of the disclosed method and compositions and together with the description, serve to explain the principles of the disclosed method and compositions.

DETAILED DESCRIPTION

Figure 1:
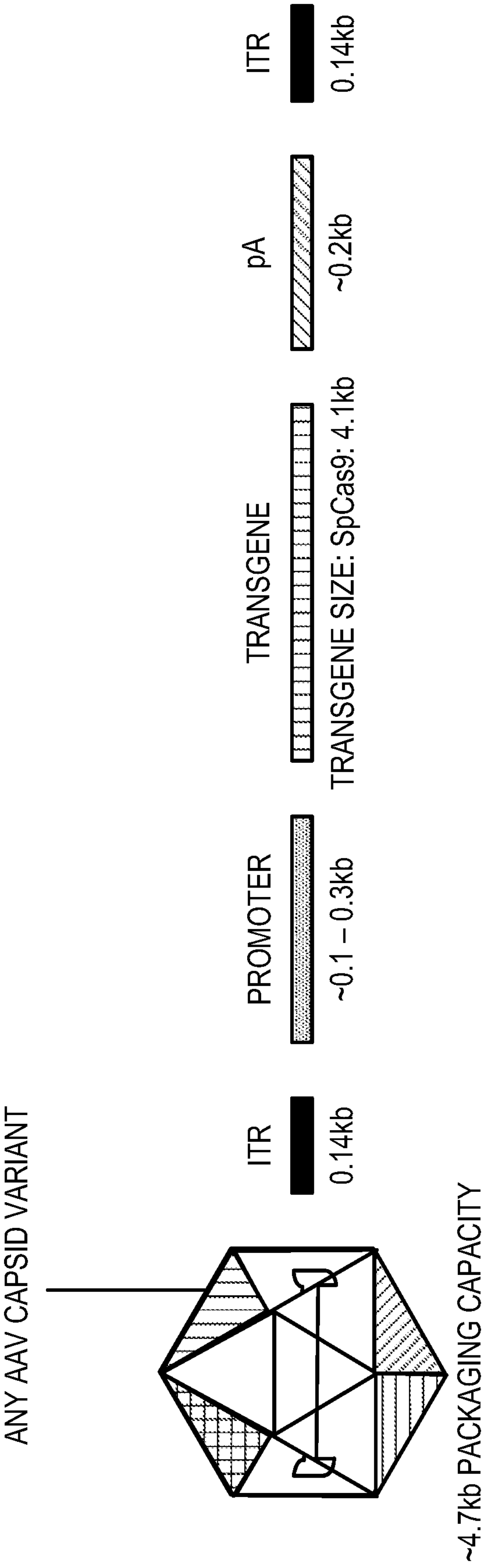
FIG. 1 shows an example operational environment.

The disclosed method and compositions may be understood more readily by reference to the following detailed description of particular embodiments and the Example included therein and to the Figures and their previous and following description.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms “a,” “an,” and “the” include plural reference unless the context clearly dictates otherwise. Thus, for example, reference to “a sequence” includes a plurality of sequences, reference to “the sequence” is a reference to one or more sequences and equivalents thereof known to those skilled in the art, and so forth.

As used herein, the terms “sequencing” or “sequencer” refer to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina or Applied Biosystems.

A "polynucleotide," "nucleic acid," "nucleic acid molecule," or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that "A" denotes adenosine, "C" denotes cytosine, "G" denotes guanosine, and "T" denotes thymidine, unless otherwise noted. The letters A, C, G, and T may be used to refer to the bases themselves, to nucleosides, or to nucleotides comprising the bases, as is standard in the art.

The term "DNA (deoxyribonucleic acid)" refers to a chain of nucleotides comprising deoxyribonucleosides that each comprise one of four nucleobases, namely, adenine (A), thymine (T), cytosine (C), and guanine (G). The term "RNA (ribonucleic acid)" refers to a chain of nucleotides comprising four types of ribonucleosides that each comprise one of four nucleobases, namely; A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

A "vector" is a replicon, such as plasmid, phage, viral construct or cosmid, to which another DNA segment may be attached. Vectors are used to transduce and express the DNA segment in cells.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III.

"Optional" or "optionally" means that the subsequently described event, circumstance, or material may or may not occur or be present, and that the description includes instances where the event, circumstance, or material occurs or is present and instances where it does not occur or is not present.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

"Exemplary" means "an example of" and is not intended to convey an indication of a preferred or ideal configuration. "Such as" is not used in a restrictive sense, but for explanatory purposes.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

B. Approaches to Design Regulatory Sequences

FIG. 1 shows a schematic diagram of an AAV vector and DNA packaged within the AAV vector. It has been determined that two inverted terminal repeat (ITR) sequences from the AAV genome, one on the 3' end and one on the 5' end, are required in the packaged DNA of an AAV gene therapy vector. Since the two ITRs of AAV are about 0.2-0.3 kb total, the foreign DNA (including the gene of interest) that can be introduced between these 2 ITRs should be smaller than 4.4 kb. By way of example, the ITRs may be 2×145 bp long (with the left ITR and the right ITR identical). When the length of foreign DNA between the 2 ITRs is close to the maximum allowed (4-4.4 kb), the packaging efficiency decreases significantly. The foreign DNA can include, but is not limited to, a promoter (with or without enhancer elements), transgene/gene of interest, polyA as shown in FIG. 1. The more foreign DNA elements that are included, the smaller the gene of interest can be. Therefore, one option for being able to increase the size of the gene of interest is to decrease the promoter size as described herein in machine learning approaches to design regulatory sequences, such as promoters.

Figure 2:
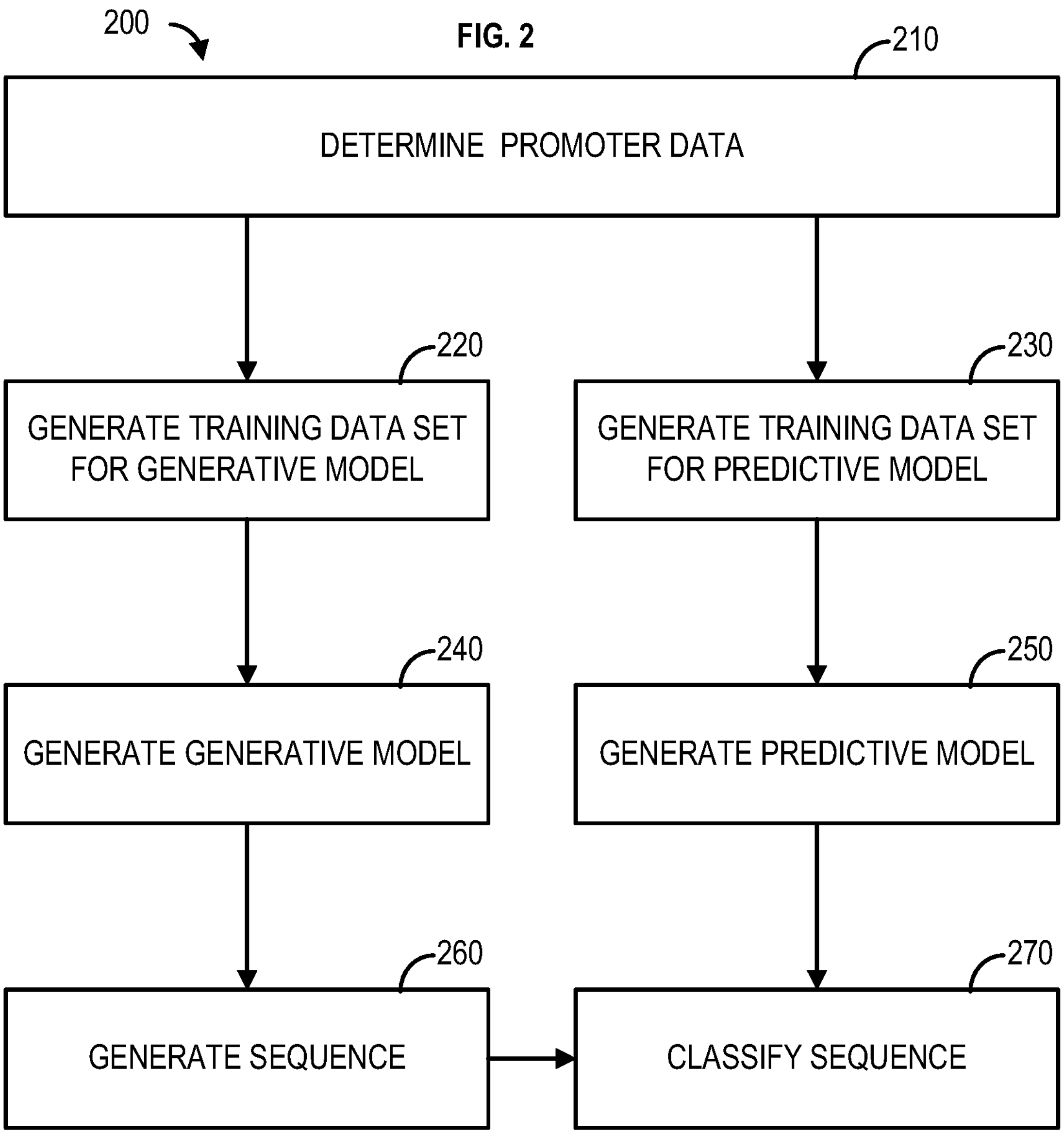
FIG. 2 shows an example method.

Described herein are machine learning approaches to design regulatory sequences. The described methods may be separated into data methods for pre-processing (generating training data) and methods for generating a predictive model and a generative model. Thus, as shown in FIG. 2, described herein is a method 200 comprising determining a promoter sequence data set at 210. Some, all, or a variant of the promoter sequence data set may be used to generate a training data set for a generative model at 220. The generative model may be configured to generate a promoter sequence based on being trained according to the promoter sequence data set. Some, all, or a variant of the promoter sequence data set may be used to generate a training data set for a predictive model at 220. The training data set for the generative model may be used to train the generative model at 240. The training data set for the predictive model may be used to train the predictive model at 240. The predictive model may serve as a quality control mechanism for the generative model. The generative model may be used to generate a core promoter sequence at 260. The predictive model may be used to classify the core promoter sequence as a core promoter or not a core promoter at 270. Accordingly, before generated core promoter sequences are tested in an experimental setting, the predictive model may be used to benchmark settings for the generative model and to test if generated sequences would be predicted to be positive for core promoter activity based on a model trained on endogenous sequences. To avoid data leakage between the predictive model and generative model, all sequences may be cross-referenced to not contain any overlap.

C. Methods for Generating Training Data

In machine learning, a training data set may be an initial set of data that serves as a baseline for further application and utilization. In some embodiments, the training data set is labeled. In some embodiments, the training data set is not labeled. One or more machine learning techniques may be used to analyze the training data set to create a model that generalizes a relationship between a feature (which may be referred to as an explanatory variable or an independent variable) and a result (which may be referred to as an objective variable or a dependent variable as needed).

Accordingly, a method is described for creating a training data set from promoter sequence data. The training data set may be created according to different methods based on the model being trained (e.g., generative model vs. predictive model). Candidate core promoter data (promoter sequence data) comprising a list of candidate core promoters for the human genome may be determined. In an embodiment, the candidate core promoter data may be downloaded from a publically available source. Candidate core promoter data may be downloaded as transcriptional start site (TSS) profiling data, for example from FANTOM5. In an embodiment, the promoter sequence data may comprise Cap Analysis of Gene Expression (CAGE) data. CAGE is a technology for mapping transcription starting sites and their promoters. CAGE enables genome-wide transcription starting detection, which results in high-throughput gene expression profiling with simultaneous identification of tissue/cell/condition specific transcriptional start sites (TSS), including promoter usage analysis. CAGE is based on preparation and sequencing of concatamers of DNA tags deriving from the initial 20 nucleotides from 5' end mRNAs, which reflect the original concentration of mRNA in the analyzed sample (RNA frequency). In CAGE data, TSS peaks across the panel of the biological states (samples) may be identified by DPI (decomposition-based peak identification), where each of the TSS peaks includes neighboring and related TSSs. The TSS peaks may be used as anchors to define promoters and as a unit of promoter-level expression analysis. A TSS summit may refer to the coordinate of the nucleotide base having the strongest signal within a given core promoter.

The promoter sequence data may be used to generate a training data set for the generative model and a training data set for the predictive model.

1. Generating Training Data for the Generative Model

In an embodiment, the promoter sequence data may be filtered, as needed. For example, the promoter sequence data may be filtered to retain only sequences by species, adult/child status, organ/tissue association, and the like. For example, the promoter sequence data may be filtered to retain only sequences associated with human, adult, and/or liver data. The promoter sequence data may be normalized. For example, a power law distribution may be used for normalization. In an embodiment, normalization may be employed if more than one library (e.g., one from adult liver and one from adult kidney) is used. Within a library, the number of sequence reads or tags may be indicative of the TSS's relative strength. However, the absolute read or tag count is not comparable between different sequencing experiments, because the total number of sequenced reads might be different for each experiment. In order to make them comparable, sequence read or tag counts are normalized. This normalization may be performed by, for example, dividing the read count by a scaling factor (e.g., the total number of reads divided by 1 million). In another example, normalization may be based on a power-law distribution. The number of TSSs that are supported by <= that number of CAGE tags follows a reverse cumulative distribution that can be approximated by a power-law distribution. For example, in a typical CAGE library, there will be 1,000 TSSs supported by 10 CAGE tags, and 10 TSSs supported by 1,000 CAGE tags. Each library may be normalized by fitting their experimentally determined distribution to a hypothetical reference distribution which is approximately similar to the libraries under analysis. Normalization may be useful, if for example, only the top 1,000 TSSs (by CAGE tag count) of both liver and kidney samples are analyzed. If the liver sample is sequenced much more deeply (more total reads), the ranking might be dominated by TSSs active in kidney or vice versa. After proper normalization, the ~500 top peaks in both kidney and liver should make up the top 1,000 TSSs in the combined sample.

The TSSs may then be distinguished from core promoters. A core promoter can be thought of as a cluster of nearby TSSs. These TSSs give rise to functionally equivalent mRNAs with slightly different 5' ends. Individual core promoters can have transcription initiation patterns that are either broad, e.g. multiple small 'peaks' of TSSs within a 100 bp window, or sharp, e.g. a single high TSS peak with several much smaller ones in a 10 bp window (this is an example). To determine the core promoter and subsequently the class, it may be determined which TSSs belong to a common cluster. Accordingly, TSSs in the promoter sequence data may be clustered and the interquantile widths of the resulting core promoters (or TSS clusters) may be determined (e.g., lower quantile=0.1, upper quantile=0.9). In an embodiment, distance-based clustering may be used, in which two independent TSSs belong to the same cluster (and thus core promoter), if the two independent TSSs are <=20 bp apart from each other. Additionally, TSSs may be required to be supported by a minimum number of reads to be included in the clustering.

After clustering, the TSS cluster (=core promoter) width may be determined. To do so, one can move along the entire cluster and count total TSS tag counts as a cumulative sum. The position at which that sum hits the lower quantile (e.g. 0.1 or 10% of the total sum) may be defined as the core promoter start, the position at which that sum hits the upper quantile (e.g. 0.9 or 90% of the total sum) may be defined as the core promoter end. The width between those two positions may be referred to as the interquantile width.

TSS's may be binned into a promoter class based on interquantile width. Promoter class may be, for example: sharp-type promoters in which transcription occurs within a narrow genomic region and broad-type promoters in which TSSs are dispersed over a larger genomic region. The core promoters may be ranked by interquantile width and the bottom half may be labeled as sharp (small width) and the top half may be labeled as broad (wide width). Sharp- and broad-type promoters are more likely to be associated with TATA boxes and CpG islands, respectively. Candidate core promoter sequences may then be determined by extending, for each TSS, the TSS summit by a number of bases in the 5' direction and a number of bases in the 3' direction. For example, to create candidate core promoter sequences that are 100 bp long, the nucleotides 49 bp in the 5' direction and 50 bp in the 3' direction may be determined. The candidate core promoter sequences may be filtered according to CAGE signal. Candidate core promoter sequences having a CAGE signal less than a threshold may be excluded, the resulting core promoter sequences may be labeled as core promoters. The threshold may be, for example, a normalized count of more than 10. In another example, the threshold may be from about, and including, 5 to about, and including 15. The count distribution may be a distribution with a very long "tail," meaning that most core promoters are supported by only a small number of CAGE tags, whereas only few core promoters are supported by many tags. Choosing a cutoff of >10 ensures that only the strongest core promoters are considered. Alternatively, a top number of peaks may be used, for example, from about, and including, 1,000 peaks to about, and including, 3,000 peaks. The number of peaks selected as a threshold represents a tradeoff between total number and strength. The more core promoters selected, the more the signal is "diluted" by including weak core promoters. This cutoff is a balance between those two opposing forces. Other example thresholds include, but are not limited to, an absolute count of 5 (~top 5000), 10 (~top 3000), 25 (~top 1500), 50 (~top 1000), and the like.

In an embodiment, a set of control sequences may be generated by shifting the set of core promoter sequences by a number of bases in the 5' or the 3' direction. For example, by shifting the candidate core promoter sequences by 50,000 bp in the 5' direction. The number of bases shifted represents a balance between staying close enough to have similar chromatin landscape, while being far enough away to not pick neighboring regulatory elements. Shifting into the 5' direction prevents shifting into the gene body (which extends into the 3' direction and in mammalian genomes is often >50 kb long). In another embodiment, a set of control sequences may be generated by selecting random sequences from the entire genome. The control sequences may be filtered to remove any control sequences that overlap with any CAGE peak, the control sequences may be labeled as not core promoters.

In an embodiment, methods are described for generating a training data set for a generative model comprising receiving genetic data. The genetic data can comprise a first plurality of nucleotide sequences. The first plurality of nucleotide sequences can comprise promoter sequences. Each nucleotide sequence of the plurality of nucleotide sequences can comprise at least one transcription start site (TSS) having an associated expression score. The associated expression score can comprise a CAGE peak. The genetic data may comprise the promoter sequence data. The genetic data may be normalized. Any normalization technique known in the art may be used, including application of a Power Law technique. The TSSs may be clustered, based on the associated expression scores and for each cluster of TSSs, an interquantile width may be determined. The interquantile width may be used to label each TSS as a sharp TSS or a broad TSS. A plurality of summit nucleotide bases may be determined in the TSSs. Determining a summit nucleotide base may comprise determining a nucleotide base having a strongest CAGE signal. For each summit nucleotide base, an associated plurality of surrounding bases may be determined. Determining the associated plurality of surrounding bases can comprise determining, for each summit nucleotide base of the plurality of summit nucleotide bases, a first plurality of nucleotide bases in the 5' direction and a second plurality of nucleotide bases in the 3' direction, thus forming a candidate core promoter sequence. The first plurality of nucleotide bases in the 5' direction can comprise 49 nucleotide bases and the second plurality of nucleotide bases in the 3' direction can comprise 50 nucleotide bases. Each summit nucleotide base and its associated plurality of surrounding bases may be stored as a second plurality of nucleotide sequences (candidate core promoter sequences) labeled as core promoters. A third plurality of nucleotide sequences may be determined from the second plurality of nucleotide sequences based on the associated expression scores satisfying a threshold. The threshold may be, for example, a normalized count of more than 10. In another example, the threshold may be from about, and including, 5 to about, and including 15. The count distribution may be a distribution with a very long "tail," meaning that most core promoters are supported by only a small number of CAGE tags, whereas only few core promoters are supported by many tags. Choosing a cutoff of >10 ensures that only the strongest core promoters are considered. Alternatively, a top number of peaks may be used, for example, from about, and including, 1,000 peaks to about, and including, 3,000 peaks. The number of peaks selected as a threshold represents a tradeoff between total number and strength. The more core promoters selected, the more the signal is "diluted" by including weak core promoters. This cutoff is a balance between those two opposing forces. Other example thresholds include, but are not limited to, an absolute count of 5 (~top 5000), 10 (~top 3000), 25 (~top 1500), 50 (~top 1000), and the like. The third plurality of nucleotide sequences may comprise a set of core promoter sequences. The set of core promoter sequences may be further filtered against any sequence containing Ns in the human genome assembly (hg19).

A set of control sequences may be generated by determining, for each nucleotide sequence of the third plurality of nucleotide sequences, an associated plurality of shifted bases, storing each associated plurality of shifted bases as a fourth plurality of nucleotide sequences labeled as not core promoters.

The set of core promoter sequences and the set of control sequences may be stored as a training data set for the generative model.

2. Generating Training Data for the Predictive Model

The promoter sequence data may be filtered by applying a CAGE peak threshold. For example, only the top CAGE peaks of the promoter sequence data may be used. In an embodiment, the CAGE peak threshold may be set so that the strength of core promoters selected for the predictive model match the strength of core promoters selected for the generative model. If the strength of core promoters match, the classification of novel generated core promoters may be more reliable. However, the number of core promoters can be lower for the predictive model, because the machine learning model employed for the predictive model (e.g., a logistic regression model) may have more bias than the machine learning model (e.g., neural network) employed for the generative model. As such the predictive model is less prone to overfitting and can be trained on fewer examples. To avoid overfitting in the generative model, more examples may be used for training than for the predictive model. The thresholds should be picked accordingly to ensure similar strength core promoters for both the predictive model and the generative model, but the input data should be picked to ensure sufficient numbers of core promoters for the generative model, which may not be as critical for the predictive model.

The filtered promoter sequence data may be further filtered to remove any sequence data that overlaps with any of the peaks of the training data set generated for the generative model. A set of core promoter sequences may then be determined by extending, for each TSS, the TSS summit by a number of bases in the 5' direction and a number of bases in the 3' direction. For example, to create core promoter sequences that are 100 bp long, the nucleotides 49 bp in the 5' direction and 50 bp in the 3' direction may be determined. The set of core promoter sequences may be further filtered against any sequence containing Ns in the human genome assembly (hg19).

A set of control sequences may be generated by shifting the set of core promoter sequences by a number of bases in the 5' or the 3' direction. For example, by shifting the candidate core promoter sequences by 50,000 bp in the 5' direction. The control sequences may be filtered to remove any control sequences that overlap with any CAGE peak and any control sequences that overlap with the set of control sequences for the generative model, the control sequences may be labeled as not core promoters.

In an embodiment, methods are described for generating a training data set for a predictive model comprising receiving genetic data. The genetic data can comprise a first plurality of nucleotide sequences. The first plurality of nucleotide sequences can comprise promoter sequences. Each nucleotide sequence of the plurality of nucleotide sequences can comprise at least one TSS having an associated expression score. The associated expression score can comprise a CAGE peak. The genetic data may comprise the promoter sequence data. The first plurality of nucleotide sequences can be filtered to remove any sequence data that overlaps with any of the peaks of the training data set generated for the generative model. A plurality of summit nucleotide bases may be determined in the TSSs. Determining a summit nucleotide bases may comprise determining a nucleotide base having a strongest CAGE signal. For each summit nucleotide base, an associated plurality of surrounding bases may be determined. Determining the associated plurality of surrounding bases can comprise determining, for each summit nucleotide base of the plurality of summit nucleotide bases, a first plurality of nucleotide bases in the 5' direction and a second plurality of nucleotide bases in the 3' direction, thus forming a candidate core promoter sequence. The first plurality of nucleotide bases in the 5' direction can comprise 49 nucleotide bases and the second plurality of nucleotide bases in the 3' direction can comprise 50 nucleotide bases. Each summit nucleotide base and its associated plurality of surrounding bases may be stored as a second plurality of nucleotide sequences (a set of core promoter sequences) labeled as core promoters. The set of core promoter sequences may be further filtered against any sequence containing Ns in the human genome assembly, for example, (hg19, hg38, and the like).

A set of control sequences may be generated by determining, for each nucleotide sequence of the second plurality of nucleotide sequences, an associated plurality of shifted bases, storing each associated plurality of shifted bases as a third plurality of nucleotide sequences (the set of control sequences) labeled as not core promoters. The set of control sequences may be filtered to remove any control sequences that overlap with any CAGE peak and any control sequences that overlap with the set of control sequences for the generative model.

The set of core promoter sequences and the set of control sequences may be stored as a training data set for the predictive model.

D. Generative Model

1. Methods for Generating the Generative Model

Disclosed herein are techniques that employ one or more recurrent neural networks (RNNs), for example a long-short term memory (LSTM) recurrent neural network (LSTM-RNN), to generate novel core promoter sequences of varying length. An LSTM-RNN model may be applied to a seed sequence to predict the next likely nucleotide given the seed sequence. The next likely nucleotide may be concatenated to the seed sequence and the resulting sequence providing back to the LSTM-RNN model to predict another next likely nucleotide given the seed sequence plus the previously determined next likely nucleotide. The LSTM-RNN model may be used to generate core promoter sequences of any length.

An RNN is a type of artificial neural network in which connections among units form a directed cycle. The RNN has an internal state that allows the network to exhibit dynamic temporal behavior. Unlike feed-forward neural networks, for instance, RNNs can use their internal memory to process arbitrary sequences of inputs. An LSTM-RNN further includes LSTM units, instead of or in addition to standard neural network units. An LSTM unit, or block, is a "smart" unit that can remember, or store, a value for an arbitrary length of time. An LSTM block contains gates that determine when its input is significant enough to remember, when it should continue to remember or forget the value, and when it should output the value.

Figure 3:
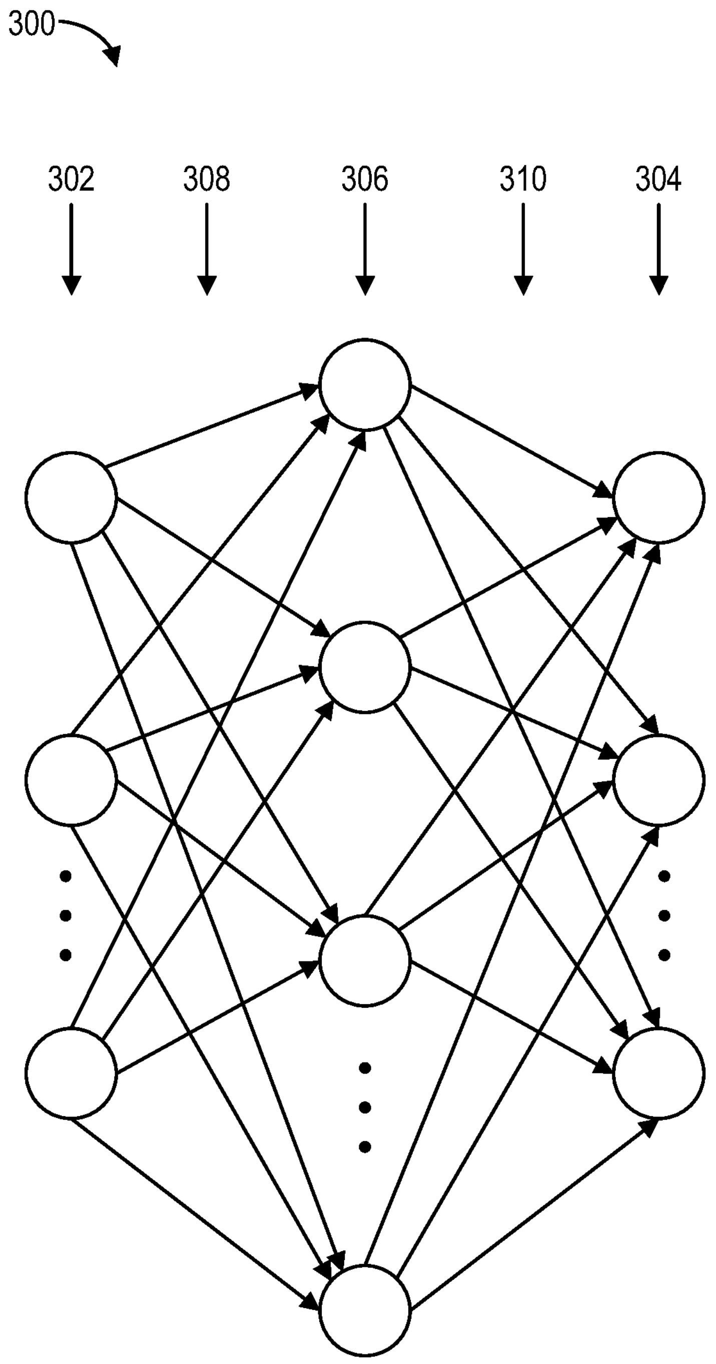
FIG. 3 shows an example method.

For clarity of the discussion, the embodiments discussed throughout this disclosure will be discussed in terms of LSTM-RNNs. However, various types of RNNs may be used in the described embodiments including, for example variants on memory cell sequencing operations (e.g., bidirectional, unidirectional, backward-looking unidirectional, or forward-looking unidirectional with a backward-looking window) or variants on the memory cell type (e.g., LSTM variants or gated recurrent units (GRU)). In a BLSTM-RNN, output depends on both past and future state information. Further, the gates of the multiplicative units allow the memory cells to store and access information over long sequences of both past and future events. Additionally, other types of positional-aware neural networks, or sequential prediction models, could be used in place of the LSTM-RNNs or BLSTM-RNNs. As depicted throughout this disclosure, an LSTM-RNN comprises an input layer, an output layer, and one or more hidden layers FIG. 3, FIG. 4A, FIG. 4B, and FIG. 5 are presented to provide an overview of a neural network 300, an RNN block 400, and an LSTM RNN block 500, respectively. FIG. 3 shows an example neural network 300. The neural network 300 includes input nodes, blocks, or units 302; output nodes, blocks, or units 304; and hidden nodes, blocks, or units 304. The input nodes 302 are connected to the hidden nodes 306 via connections 308, and the hidden nodes 306 are connected to the output nodes 304 via connections 310.

The input nodes 302 correspond to input data, whereas the output nodes 304 correspond to output data as a function of the input data. For instance, the input nodes 302 can correspond to an input sequence and the output nodes 104 can correspond to an output sequence or nucleotide. The nodes 306 are hidden nodes in that the neural network model itself generates the nodes. Just one layer of nodes 306 is depicted, but in actuality there is usually more than one layer of nodes 306.

Therefore, to construct the neural network 300, training data in the form input data that has been manually or otherwise already mapped to output data is provided to a neural network model, which generates the network 300. The model thus generates the hidden nodes 306, weights of the connections 310 between the input nodes 302 and the hidden nodes 306, weights of the connections 310 between the hidden nodes 306 and the output nodes, and weights of connections between layers of the hidden nodes 306 themselves. Thereafter, the neural network 300 can be employed against input data for which output data is unknown to generate the desired output data.

An RNN is one type of neural network. A general neural network does not store any intermediary data while processing input data to generate output data. By comparison, an RNN does persist data, which can improve its classification ability over a general neural network that does not.

Figure 4A:
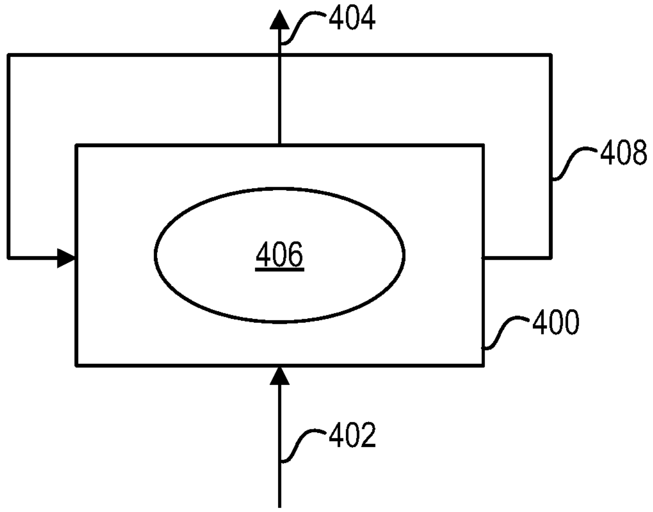
FIG. 4A shows a compact notation an example RNN block.

FIG. 4A shows a compact notation an example RNN block 400, which typifies a hidden node 306 of the neural network 300 that is an RNN. The RNN block 400 has an input connection 402, which may be a connection 308 of FIG. 3 that leads from one of the input nodes 302, or which may be a connection that leads from another hidden node 306. The RNN block 400 likewise has an output connection 404, which may be a connection 310 of FIG. 3 that leads to one of the output nodes 304, or which may be a connection that leads to another hidden node 306.

The RNN block 400 generally is said to including processing 406 that is performed on (at least) the information provided on the input connection 402 to yield the information provided on the output connection 404. The processing 406 is typically in the form of a function. For instance, the function may be an identity activation function, mapping the output connection 404 to the input connection 402. The function may be a sigmoid activation function, such as a logistic sigmoid function, which can output a value within the range (0, 1) based on the input connection 402. The function may be a hyperbolic tangent function, such as a hyperbolic logistic tangent function, which can output a value within the range (−1, 1) based on the input connection 402.

The RNN block 400 also has a temporal loop connection 408 that leads back to a temporal successor of itself. The connection 408 is what renders the RNN block 400 recurrent, and the presence of such loops within multiple nodes is what renders the neural network 300 recurrent. The information that the RNN block 400 outputs on the connection 404 (or other information) therefore can persist on the connection 408, on which basis new information received on the connection 402 can be processed. That is, the information that the RNN block 400 outputs on the connection 404 is merged, or concatenated, with information that the RNN block 400 next receives on the input connection 402, and processed via the processing 406.

Figure 4B:
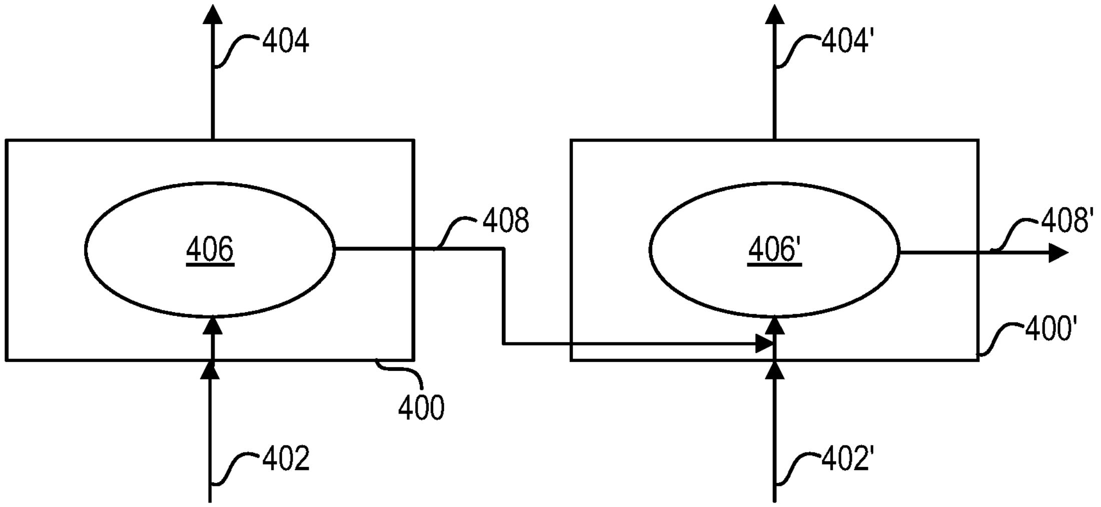
FIG. 4B shows an expanded notation of the RNN block.

FIG. 4B shows an expanded notation of the RNN block 400. The RNN block 400' and the connections 402', 404', 406', 408' are the same RNN block 400 and the connections 402, 404, 406, 408, but at a temporally later time. FIG. 4B thus illustrates that the RNN block 400' at the later time receives the information provided on the connection 406 provided by the (same) RNN block 400 at an earlier time. The RNN block 400' at the later time can itself provide information to itself at an even later time on the connection 406'.

An LSTM-RNN is one type of RNN. A general RNN in theory can persist information over both the short term and the long term. However, in practice, such RNNs have not been proven capable of persisting information over the long term. More technically, a general RNN is practically incapable of learning long-term dependencies, which means that the RNN is unable to process information based on information that it previously processed a relatively long. By comparison, an LSTM-RNN is a special type of RNN that can learn long-term dependencies, and therefore a type of RNN that can persist information over the long term.

Figure 5:
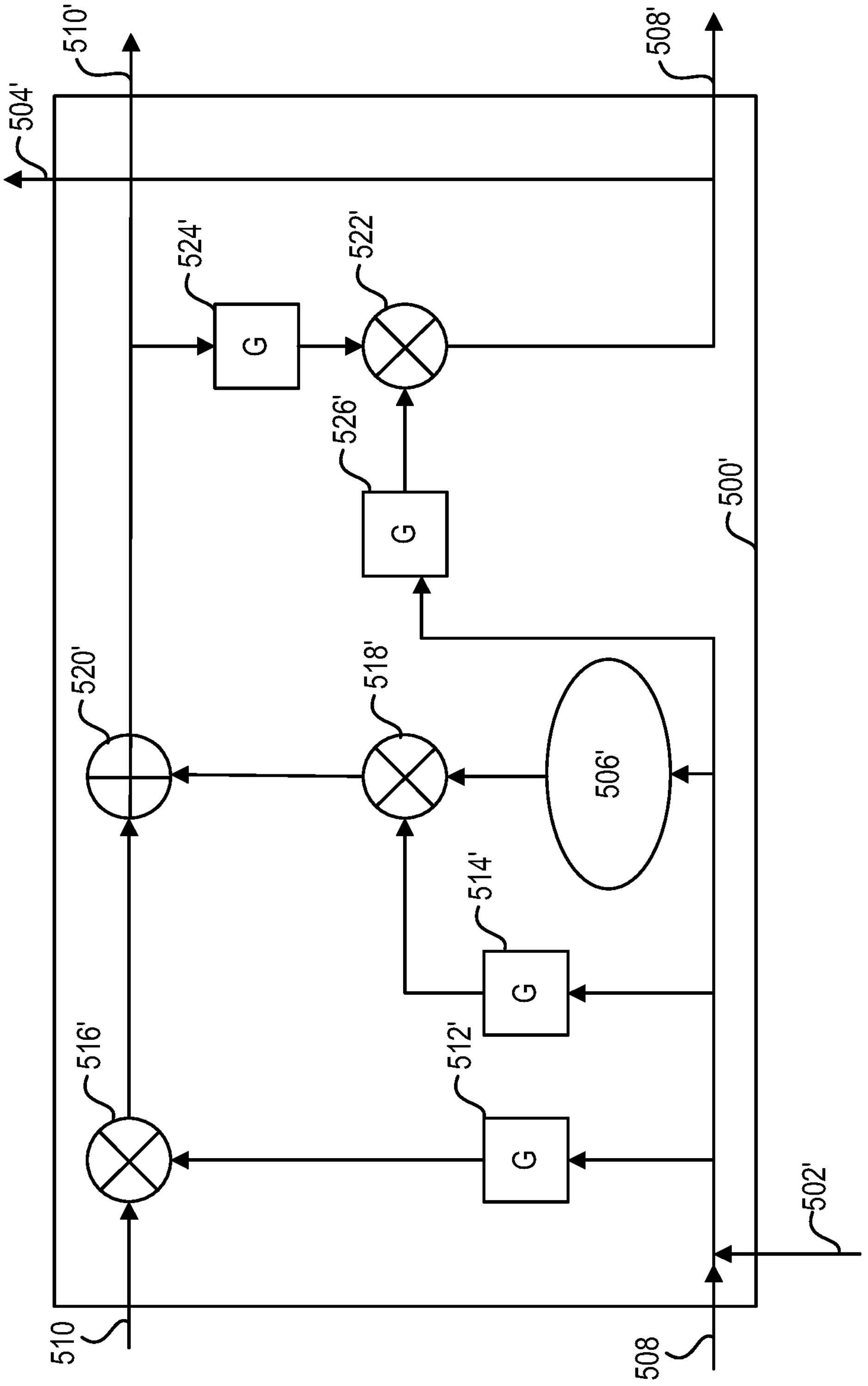
FIG. 5 shows an example LSTM-RNN block.

FIG. 5 shows an example LSTM-RNN block 500'. The LSTM-RNN block 500' has an input connection 502', an output connection 504', and processing 506', comparable to the connections 402/402' and 404/404', and processing 406/406' of the RNN block 400/400' of FIG. 4A and FIG. 4B. However, rather than having a single temporal loop connection 408/408' that connects temporal instances of the RNN block 400/400', the LSTM-RNN block 500' has two temporal loop connections 508' and 510' over which information persists among temporal instances of the LSTM-RNN block 500.

The information on the input connection 502' is merged with the persistent information provided on the connection 508 from a prior temporal instance of the LSTM-RNN block and undergoes the processing 506'. How the result of the processing 506' is combined, if at all, with the persistent information provided on the connection 510 from the prior temporal instance of the LSTM-RNN block is controlled via gates 512' and 514'. The gate 512', operating on the basis of the merged information of the connections 502' and 508, controls an element-wise product operator 516' permitting the persistent information on the connection 510 to pass (or not). The gate 514', operating on the same basis, controls an element-wise operator 518' permitting of the output of the processing 506' to pass (or not).

The outputs of the operators 516' and 518' is summed via an addition operator 520', and is passed as the persistent information on the connection 510' of the current instance of the LSTM-RNN block 500'. Therefore, the extent to which the persistent information on the connection 510' reflects the persistent information on the connection 510 and the extent to which this information on the connection 510' reflects the output of the processing 506' is controlled by the gates 512' and 514'. As such, information can persist across or over multiple temporal instances of the LSTM-RNN block as desired.

The output of the current instance of the LSTM-RNN block 500' is itself provided on the connection 504' to the next layer of the RNN, and also persists to the next temporal instance of the LSTM-RNN block on connection 508'. This output is provided by another element-wise product operator 522', which passes a combination of the information also provided on the connection 510' and the merged information on the connections 502' and 508 as controlled by the gates 524' and 526', respectively. In this way, then, the LSTM-RNN block 500' of FIG. 5 can persist both long-term as well as short-term information.

Figure 6:
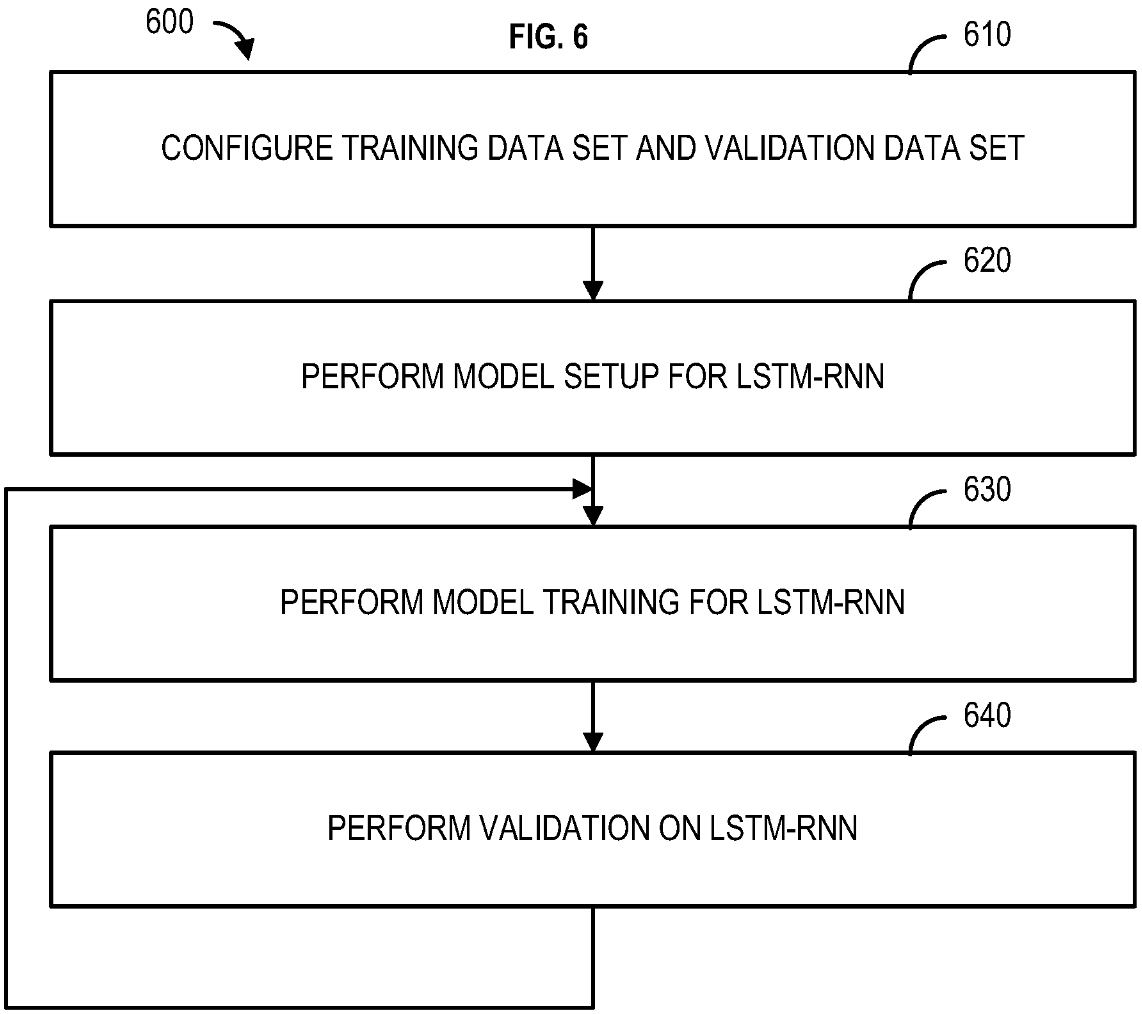
FIG. 6 shows an example method.

As described in further detail below, one or more (RNNs), for example an LSTM-RNN, may be used to determine a promoter sequence. The LSTM-RNN, via a training process, provides a model that predicts a set of parameters based on a set of input features. FIG. 6 depicts an example method 600 for training an LSTM-RNN. In some variations, the training process may be performed using specialized software (e.g., keras, Tensforflow script, the CURRENNT toolkit, or a modified version of an off-the-shelf toolkit) and/or specialized hardware.

At step 610, a computing device may determine a training data set as described herein. The training data set may comprise a set of core promoter sequences labeled as core promoters and a set of control sequences labeled as not core promoters. The training data set may be used for training and validating the LSTM-RNN. In some variations, a first portion of the training data may be used for training and a second portion of the training data may be used for testing/validation. The set of core promoter sequences may be split sequences of the different classes (sharp/broad) into pairs of seed sequences and prediction targets. The seed sequence may comprise a nucleotide sequence of any length, for example 10 nucleotides. The prediction target may comprise the nucleotide immediately following the seed sequence. Seed sequence/prediction target pairs may be generated by splitting the core promoter sequences using a sliding window approach with a step size of 1. The sequence pairs may then be vectorized using a numerical encoding (e.g., "A": 0, "C": 1, "G": 2, "T": 3). The different classes of core promoters differ fundamentally in their biology. Typically, only the "sharp" promoter class is used in plasmid based or viral vector based transgenes. The two classes differ in their sequence content, meaning that the two classes cannot be mixed for training or sequence generation. In other words, if core promoters from both classes were used for training, the signal from core promoter motifs that are typically found in 'sharp' core promoters would be diluted, potentially leading to the generation of non-functional sequences. Instead, the two types are separated, and then new sequences may be generated based on two separately trained models thus generating novel instances of "sharp" or "broad" core promoters. Which type of core promoter is generated depends on the application, but will most commonly be of the type "sharp." In conclusion, the separation is less relevant for applications (because commonly only sharp core promoters are used), but more relevant for proper training given that a mix of sharp and broad would dilute out the correct signal. However, the separate classes may also be used to generate a 'broad' type core promoter.

At step 620, the computing device may perform model setup for the LSTM-RNN. Model setup may include initializing weights of the connections for the LSTM-RNN. In some arrangements, pre-training may be performed to initialize the weights. In others, the weights may be initialized according to a distribution scheme. One distribution scheme includes randomizing the values of the weights according to a normal distribution with mean equal to 0 standard deviation equal to 0.1. In an embodiment, each nucleotide may be associated with a weight. For example, the weights may be assigned as: A: 0.2, C:0.05, G:0.6, T:0.15

At step 630, the computing device may perform model training on the LSTM-RNN. In some variations, the model training may include performing one or more training techniques including, for example, steepest descent, stochastic gradient descent, or resilient backpropagation (RPROP). The training technique applies the training set to the model and adjusts the model. To speed up the model training, parallel training may be performed. For example, the training set may be split into batches of 100 sequences that are processed in parallel with other batches.

At step 640, the computing device may perform model validation on the LSTM-RNN. In some variations, the validation set may be applied to the trained model and heuristics may be tracked. The heuristics may be compared to one or more stop conditions. If a stop condition is satisfied, the training process may end. If none of the one or more stop conditions are satisfied, the model training of step 630 and validation of step 640 may be repeated. Each iteration of steps 630 and 640 may be referred to as a training epoch. Some of the heuristics that may be tracked include sum squared errors (SSE), weighted sum squared error (WSSE), regression heuristics, or number of training epochs.

2. Methods for Using the Generative Model

Figure 7:
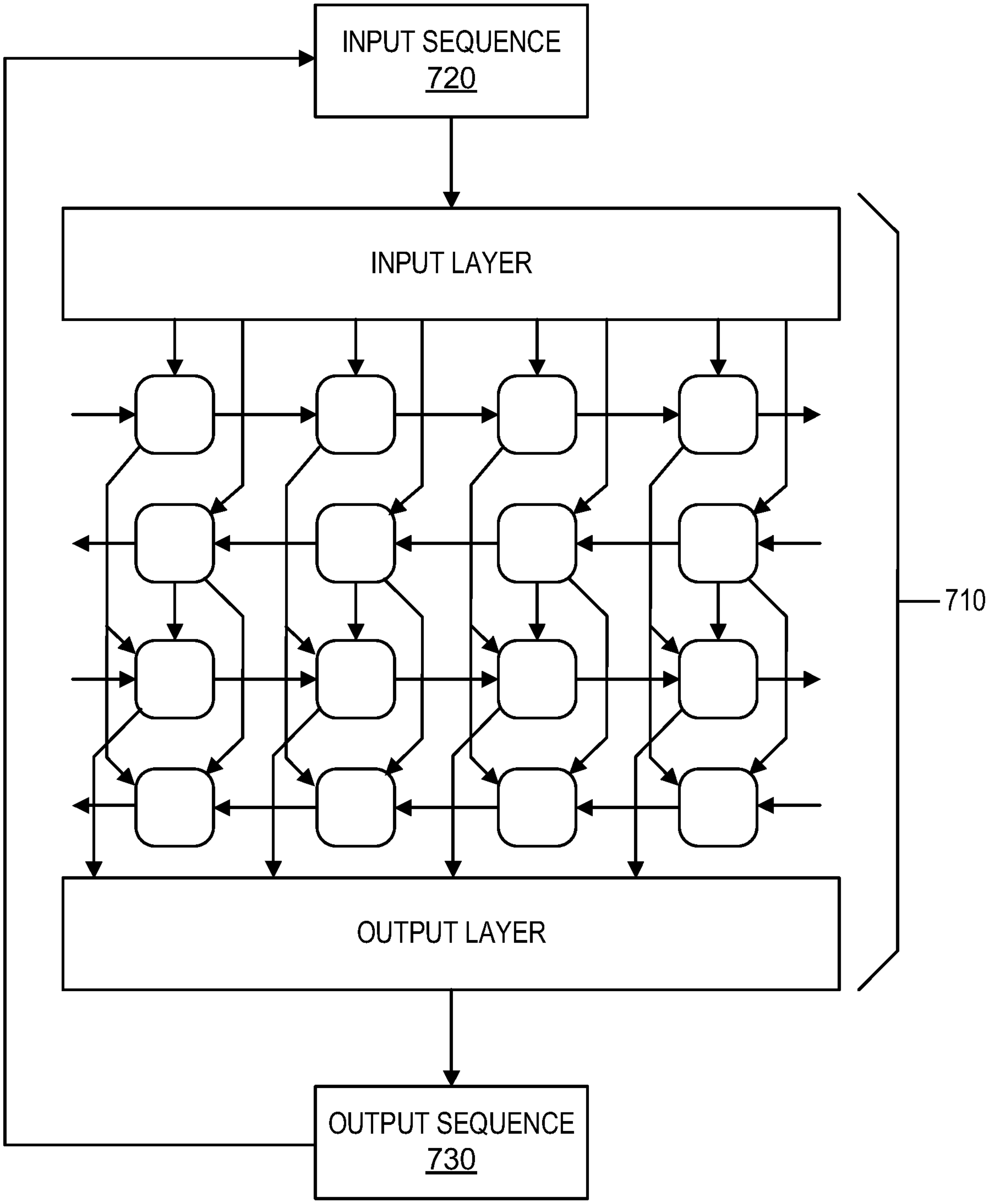
FIG. 7 shows an example method.

FIG. 7 depicts an example flow that uses a trained LSTM-RNN 710 for determining a promoter sequence. The LSTM-RNN 710 may be configured to receive an input sequence 720 (e.g., a "seed"). The input sequence 720 may comprise a nucleotide sequence. The nucleotide sequence may comprise a promoter sequence (e.g., a core promoter sequence). The input sequence 720 may have a length. The length may be, for example, from about 5 nucleotides to about 100 nucleotides. The input sequence 720 may be 10 nucleotides long. Other input sequence lengths are contemplated, for example, 1, 2, 3, 4, 5, 6, 7, 8, 9, 11, 12, 13, 14, 15, 16, 17, 18, 19, or 20 nucleotides long. In an embodiment, the source of the input sequence 720 may be a random sequence or the first 10 nt (or any other input sequence length) of a randomly chosen core promoter from the training data set. In an embodiment, the 10 nt (or any other input sequence length) leading up to a certain core promoter motif from a real world example may be selected as the input sequence 720, in order to enforce the generation of core promoters with that motif. In another embodiment, a random sequence may be used as the input sequence and the output sequences may be screened for the existence of a certain motif.

The input sequence 720 is input to the LSTM-RNN 710 which processes the input sequence 720 via an input layer, one or more hidden layers, and an output layer. The LSTM-RNN 710 outputs the likely next nucleotide via the output layer. Thus, the LSTM-RNN 710 may be configured to predict a likely next nucleotide which may be appended to the input sequence 720 to generate an output sequence 730. The LSTM-RNN 710 may be configured to predict the likely next nucleotide based on nucleotide probabilities. The nucleotide probabilities may be, for example, A: 0.2, C:0.05, G:0.6, T:0.15. The LSTM-RNN 710 may be configured to take as input the generated output sequence 730, effectively treating the output sequence 730 as a new input sequence 720. The LSTM-RNN 710 may be configured to repeatedly predict the likely next nucleotide until a desired length is achieved for the output sequence 730. The desired output length may be, for example, from about 20 nucleotides to about 100 nucleotides. The desired output length may be 50 nucleotides. The LSTM-RNN 710 produces a probability distribution of the next nucleotide in a new promoter sequence given a promoter sequence of previous nucleotides. This allows the LSTM-RNN 710 to produce a new promoter sequence one nucleotide at a time. In an embodiment, any number of core promoters can be generated, which can then be screened for certain aspects, such as GC content or core promoter motif content (similar features as used in the predictive model).

Figure 8:
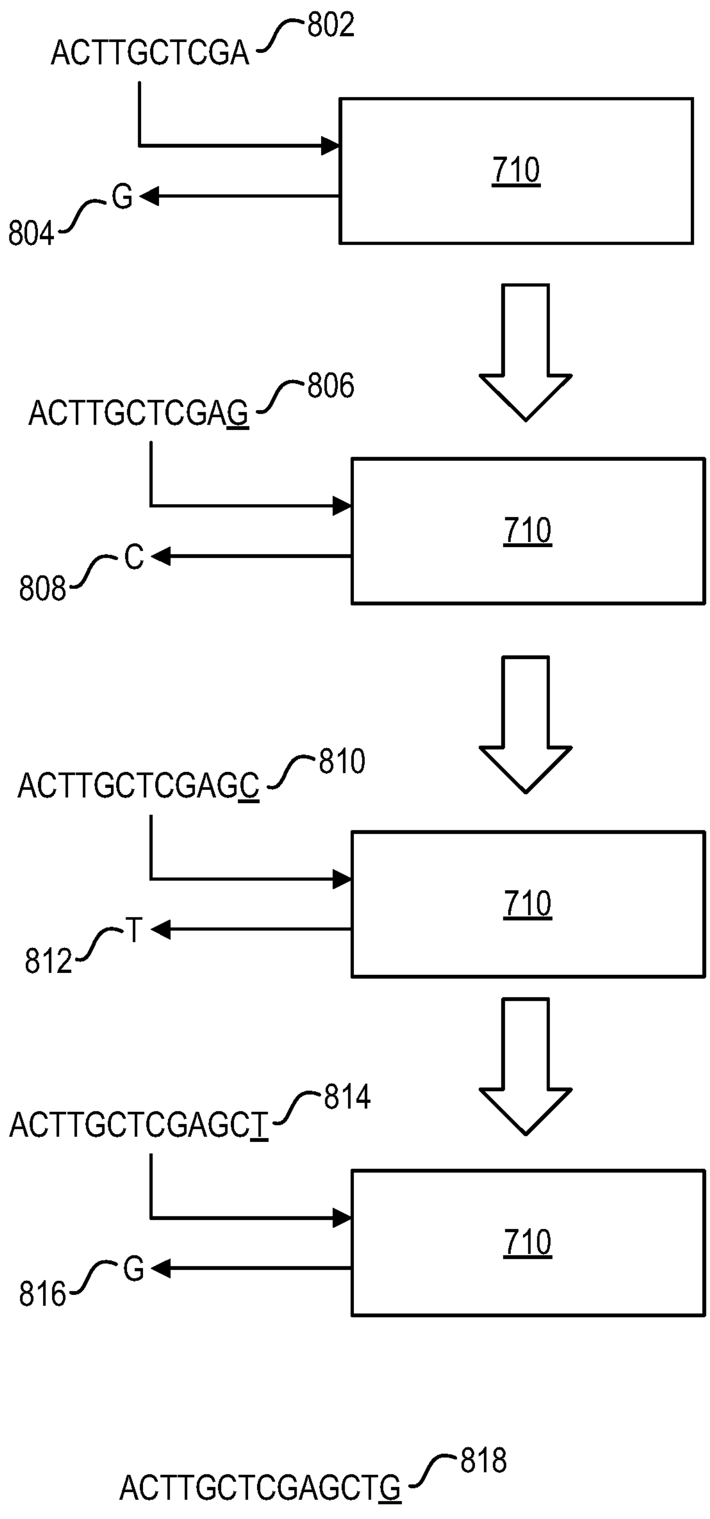
FIG. 8 shows an example method. 802 shows SEQ ID NO:1; 806 shows SEQ ID NO:2; 810 shows SEQ ID NO:3; 814 shows SEQ ID NO:4; 818 shows SEQ ID NO:5.

FIG. 8 is a visual depiction of generating a core promoter sequence. A seed sequence 802 may be input into the LSTM-RNN 710 and a desired final core promoter sequence length may be specified. In the example of FIG. 8, the seed sequence 802 is 10 nucleotides long and the desired final core promoter sequence length is 14 nucleotides. The LSTM-RNN 710 may predict, given the seed sequence 802, a next likely nucleotide 804. The next likely nucleotide 804 may be added (concatenated) to the seed sequence 802 to create sequence 806. The LSTM-RNN 710 may predict, given at least a portion of the sequence 806, a next likely nucleotide 808. For example, a sliding window of n nucleotides may be used to predict the next likely nucleotide 808. The sliding window may be, for example, 5, 6, 7, 8, 9, 10, 11, 12, 13, 14, or 15 nucleotides long. The next likely nucleotide 808 may be added (concatenated) to the sequence 806 to create sequence 810. The LSTM-RNN 710 may predict, given at least a portion of the sequence 810, a next likely nucleotide 812. For example, the sliding window of n nucleotides may be used to predict the next likely nucleotide 812. The next likely nucleotide 812 may be added (concatenated) to the sequence 810 to create sequence 814. The LSTM-RNN 710 may predict, given at least a portion of the sequence 814, a next likely nucleotide 816. For example, the sliding window of n nucleotides may be used to predict the next likely nucleotide 816. The next likely nucleotide 816 may be added (concatenated) to the sequence 816 to create a final core promoter sequence 818. The length of the final core promoter sequence 818 is equal to the desired final core promoter sequence length and the final core promoter sequence 818 may be output as a core promoter.

In an embodiment, methods are described comprising: a) receiving a nucleotide sequence and a sequence length; b) providing, to a trained generative model, the nucleotide sequence; c) determining, based on the generative model, a next nucleotide associated with the nucleotide sequence; d) appending the next nucleotide to the nucleotide sequence; e) repeating b-d until a length of the nucleotide sequence equals the sequence length; and f) outputting the nucleotide sequence as a core promoter sequence. The sequence length can be from about 50 nucleotides to about 100 nucleotides.

As described herein, methods and systems are provided for generating core promoter sequences of a defined length and/or with a defined sequence content. Generated core promoter sequences can be used in any kind of transgene, for example: viral vectors such as AAV, adeno or lentivirus, both in preclinical research and gene therapy; genome editing vectors such as those driving Cas9 expression, Cre-lox, TALENs or zinc finger nucleases; luminescence or fluorescent reporter plasmids; antibody expression plasmids for high yield; cloning and engineering plasmids; chemogenetics (such as DREADDs) and optogenetics. In some aspects, a construct or vector comprising one or more of the generated core promoters can be referred to as a nucleic acid construct. Thus, the disclosed nucleic acid constructs can comprise the generated core promoters and one or more transgenes. In some aspects, the disclosed nucleic acid constructs, can be any expression vector, viral or non-viral. In some aspects, nucleic acid constructs can be linear or circular. Circular nucleic acid constructs can be referred to as plasmids or vectors.

Core promoter sequences thus generated may be used in transgenes on viral vectors for gene therapy. Currently, AAV is the gold standard of gene therapy, but has a very limited genome size, meaning that any element that is used on an AAV vector should be optimized for size. The coding sequence for some of the transgenes, for example Cas9, cannot be optimized for size, but other regulatory elements can be (such as the core promoter). So, instead of using an endogenous core promoter that might be 100 nt long, the disclosed methods and system can generate a core promoter that is 50 nt long, has a defined motif content and is thus even more efficient at driving gene expression than any endogenous core promoter.

In an embodiment, the sequence content of generated core promoter sequences may be defined to avoid an innate immune response in gene therapy settings. Core promoters often have a high content of CpG dinucleotides, which can trigger a TLR based innate immune response. Using the described generative model, core promoter sequences can be generated that lack CpG dinucleotides.

The methods may further comprising engineering a promoter based on the core promoter sequence. The methods may further comprising inserting the promoter into a nucleic acid construct. Inserting the promoter into the nucleic acid construct comprises inserting the promoter into the nucleic acid construct upstream of a transgene to drive expression of the transgene. The methods may further comprise producing an adeno associated virus or a lentivirus comprising the nucleic acid construct. In some aspects, any known viral vector can be produced comprising the disclosed nucleic acid constructs. In some aspects, the methods may comprise producing any known non-viral vector (e.g. DNA based vectors) comprising the generated core promoters.

The term "expression vector" includes any vector, (e.g., a plasmid, cosmid or phage chromosome) containing a transgene in a form suitable for expression by a cell (e.g., linked to a transcriptional control element). In some aspects, "plasmid" and "vector" are used interchangeably, as a plasmid is a commonly used form of DNA vector. Moreover, the invention is intended to include other vectors which serve equivalent functions.

E. Predictive Model

1. Methods for Generating the Predictive Model

Figure 9:
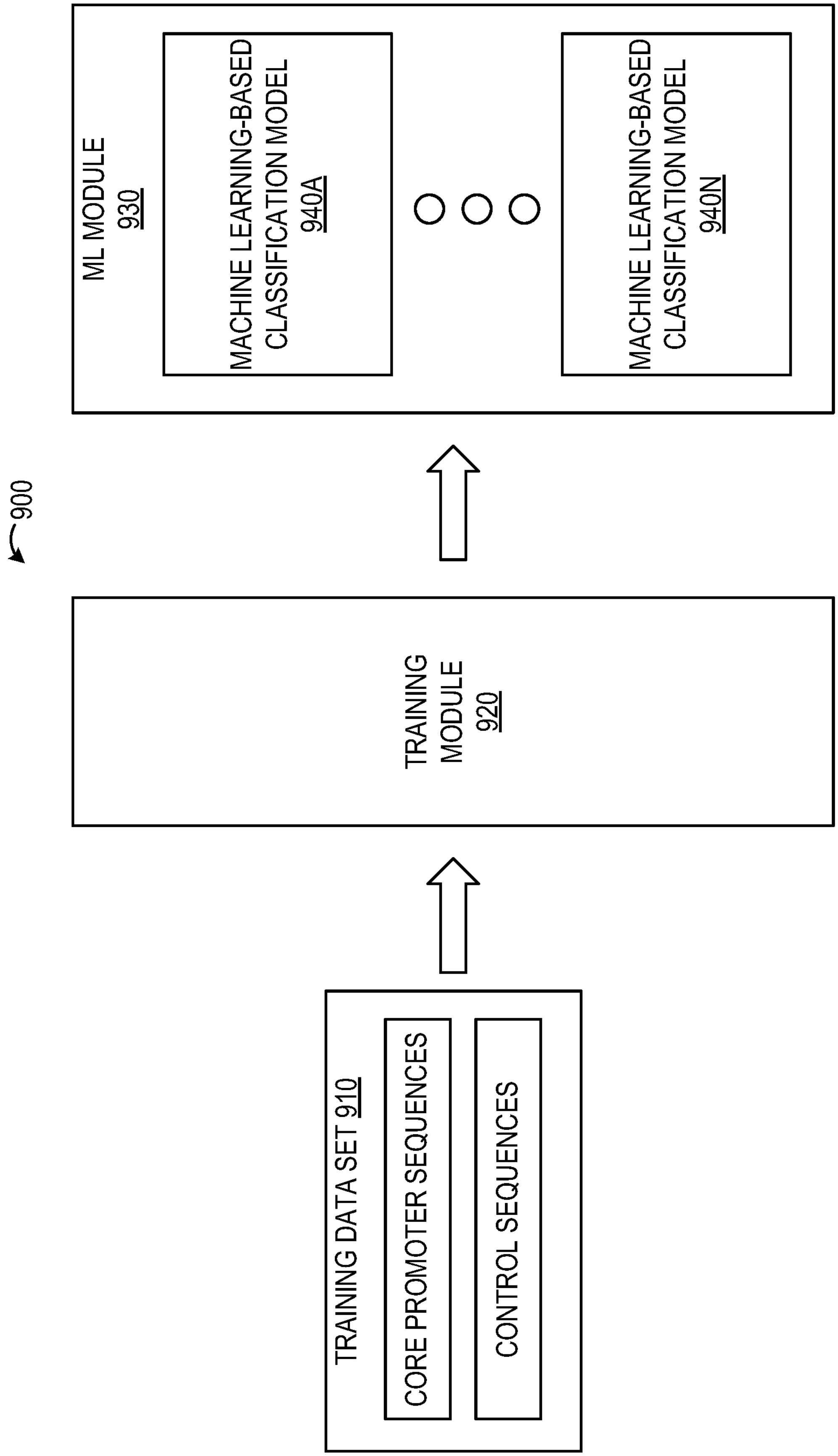
FIG. 9 shows an example method.

Turning now to FIG. 9, methods are described for generating a predictive model. The methods described may use machine learning ("ML") techniques to train, based on an analysis of one or more training data sets 910 by a training module 920, at least one ML module 930 that is configured to predict a promoter status (e.g., promoter/non-promoter) for a given sequence.

The training data set 910 may comprise a set of core promoter sequences, labeled as core promoter sequences (YES) and a set of control sequences, labeled as not core promoter sequences (NO). Such data may be derived in whole or in part from the promoter sequence data as described herein.

A subset of the set of core promoter sequences and the set of control sequences may be randomly assigned to the training data set 910 or to a testing data set. In some implementations, the assignment of data to a training data set or a testing data set may not be completely random. In this case, one or more criteria may be used during the assignment. In general, any suitable method may be used to assign the data to the training or testing data sets, while ensuring that the distributions of yes and no labels are somewhat similar in the training data set and the testing data set.

The training module 920 may train the ML module 930 by extracting a feature set from a plurality of core promoter sequences (e.g., labeled as yes) and/or a plurality of control sequences (e.g., labeled as no) in the training data set 910 according to one or more feature selection techniques. The training module 920 may train the ML module 930 by extracting a feature set from the training data set 910 that includes statistically significant features of positive examples (e.g., labeled as being yes) and statistically significant features of negative examples (e.g., labeled as being no).

The training module 920 may extract a feature set from the training data set 910 in a variety of ways. The training module 920 may perform feature extraction multiple times, each time using a different feature-extraction technique. In an example, the feature sets generated using the different techniques may each be used to generate different machine learning-based classification models 940. For example, the feature set with the highest quality metrics may be selected for use in training. The training module 920 may use the feature set(s) to build one or more machine learning-based classification models 940A-940N that are configured to indicate whether a new sequence (e.g., with an unknown promoter status) is likely or not likely a promoter.

Figure 10:
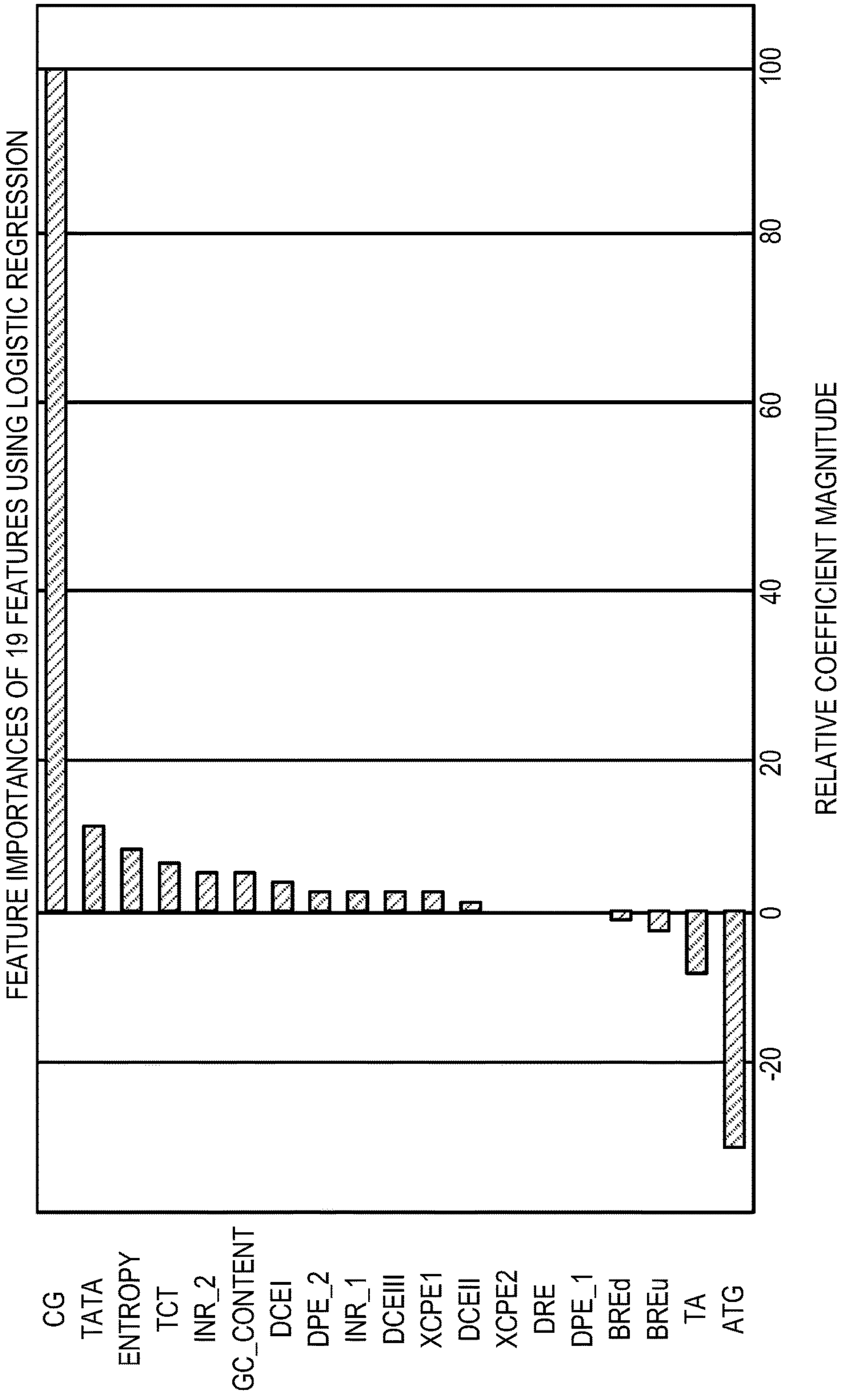
FIG. 10 shows example features of a predictive model.

The training data set 910 may be analyzed to determine any dependencies, associations, and/or correlations between features and the yes/no labels in the training data set 910. The identified correlations may have the form of a list of features that are associated with different yes/no labels. The term "feature," as used herein, may refer to any characteristic of an item of data that may be used to determine whether the item of data falls within one or more specific categories. By way of example, the features described herein may comprise one or more sequence patterns, GC content, CpG content, known core promoter sequence motifs, ATG frequency, and/or relative entropy. For known core promoter sequence motif occurrences, the relative positioning with respect to the TSS may also be taken into account. Relative entropy is a measure of how similar a sequence is to a random sequence based on fixed nucleotide distributions (core promoter sequences are less random). Example probabilities for random DNA are: Probabilities for random DNA: A: 0.3, C: 0.2, T: 0.2, G: 0.3. FIG. 10 shows the relative significance of various features in predicting promoter status. For example, CpG dinucleotide content has the strongest positive correlation with core promoter identity. Random DNA has relatively few CpGs, whereas core promoters can have many (a subset of core promoters is called CpG islands). Presence or absence of a TATA box is also significant.

Returning to FIG. 9, a feature selection technique may comprise one or more feature selection rules. The one or more feature selection rules may comprise a feature occurrence rule. The feature occurrence rule may comprise determining which features in the training data set 910 occur over a threshold number of times and identifying those features that satisfy the threshold as features.

A single feature selection rule may be applied to select features or multiple feature selection rules may be applied to select features. The feature selection rules may be applied in a cascading fashion, with the feature selection rules being applied in a specific order and applied to the results of the previous rule. For example, the feature occurrence rule may be applied to the training data set 910 to generate a first list of features. A final list of features may be analyzed according to additional feature selection techniques to determine one or more feature groups (e.g., groups of features that may be used to predict promoter status). Any suitable computational technique may be used to identify the feature groups using any feature selection technique such as filter, wrapper, and/or embedded methods. One or more feature groups may be selected according to a filter method. Filter methods include, for example, Pearson's correlation, linear discriminant analysis, analysis of variance (ANOVA), chi-square, combinations thereof, and the like. The selection of features according to filter methods are independent of any machine learning algorithms. Instead, features may be selected on the basis of scores in various statistical tests for their correlation with the outcome variable (e.g., yes/no).

As another example, one or more feature groups may be selected according to a wrapper method. A wrapper method may be configured to use a subset of features and train a machine learning model using the subset of features. Based on the inferences that drawn from a previous model, features may be added and/or deleted from the subset. Wrapper methods include, for example, forward feature selection, backward feature elimination, recursive feature elimination, combinations thereof, and the like. As an example, forward feature selection may be used to identify one or more feature groups. Forward feature selection is an iterative method that begins with no feature in the machine learning model. In each iteration, the feature which best improves the model is added until an addition of a new variable does not improve the performance of the machine learning model. As an example, backward elimination may be used to identify one or more feature groups. Backward elimination is an iterative method that begins with all features in the machine learning model. In each iteration, the least significant feature is removed until no improvement is observed on removal of features. Recursive feature elimination may be used to identify one or more feature groups. Recursive feature elimination is a greedy optimization algorithm which aims to find the best performing feature subset. Recursive feature elimination repeatedly creates models and keeps aside the best or the worst performing feature at each iteration. Recursive feature elimination constructs the next model with the features remaining until all the features are exhausted. Recursive feature elimination then ranks the features based on the order of their elimination.

As a further example, one or more feature groups may be selected according to an embedded method. Embedded methods combine the qualities of filter and wrapper methods. Embedded methods include, for example, Least Absolute Shrinkage and Selection Operator (LASSO) and ridge regression which implement penalization functions to reduce overfitting. For example, LASSO regression performs L1 regularization which adds a penalty equivalent to absolute value of the magnitude of coefficients and ridge regression performs L2 regularization which adds a penalty equivalent to square of the magnitude of coefficients.

After the training module 920 has generated a feature set(s), the training module 920 may generate a machine learning-based classification model 940 based on the feature set(s). A machine learning-based classification model may refer to a complex mathematical model for data classification that is generated using machine-learning techniques. In one example, the machine learning-based classification model 940 may include a map of support vectors that represent boundary features. By way of example, boundary features may be selected from, and/or represent the highest-ranked features in, a feature set.

The training module 920 may use the feature sets determined or extracted from the training data set 910 to build a machine learning-based classification model 940A-940N for each classification category (e.g., yes, no). In some examples, the machine learning-based classification models 940A-940N may be combined into a single machine learning-based classification model 940. Similarly, the ML module 930 may represent a single classifier containing a single or a plurality of machine learning-based classification models 940 and/or multiple classifiers containing a single or a plurality of machine learning-based classification models 940.

The features may be combined in a classification model trained using a machine learning approach such as discriminant analysis; decision tree; a nearest neighbor (NN) algorithm (e.g., k-NN models, replicator NN models, etc.); statistical algorithm (e.g., Bayesian networks, etc.); clustering algorithm (e.g., k-means, mean-shift, etc.); neural networks (e.g., reservoir networks, artificial neural networks, etc.); support vector machines (SVMs); logistic regression algorithms; linear regression algorithms; Markov models or chains; principal component analysis (PCA) (e.g., for linear models); multi-layer perceptron (MLP) ANNs (e.g., for non-linear models); replicating reservoir networks (e.g., for non-linear models, typically for time series); random forest classification; a combination thereof and/or the like. The resulting ML module 930 may comprise a decision rule or a mapping for each feature to assign an promoter status to a new sequence.

In an embodiment, the training module 920 may train the machine learning-based classification models 940 as a convolutional neural network (CNN). The CNN comprises at least one convolutional feature layer and three fully connected layers leading to a final classification layer (softmax). The final classification layer may finally be applied to combine the outputs of the fully connected layers using softmax functions as is known in the art.

The feature(s) and the ML module 930 may be used to predict the promoter statuses of sequences in the testing data set. In one example, the prediction result for each sequence includes a confidence level that corresponds to a likelihood or a probability that the sequence is a promoter. The confidence level may be a value between zero and one, and it may represent a likelihood that the sequence belongs to a yes/no promoter status. In one example, when there are two statuses (e.g., yes and no), the confidence level may correspond to a value p, which refers to a likelihood that a particular sequence belongs to the first status (e.g., yes). In this case, the value 1−p may refer to a likelihood that the particular sequence belongs to the second status (e.g., no). In general, multiple confidence levels may be provided for each sequence in the testing data set and for each feature when there are more than two statuses. A top performing feature may be determined by comparing the result obtained for each test sequence with the known yes/no promoter status for each test sequence. In general, the top performing feature will have results that closely match the known yes/no promoter statuses. The top performing feature(s) may be used to predict the yes/no promoter status of a sequence. For example, a new sequence may be determined/received. The new sequence may be provided to the ML module 930 which may, based on the top performing feature(s), classify the new sequence as either a promoter (yes) or not a promoter (no).

Figure 11:
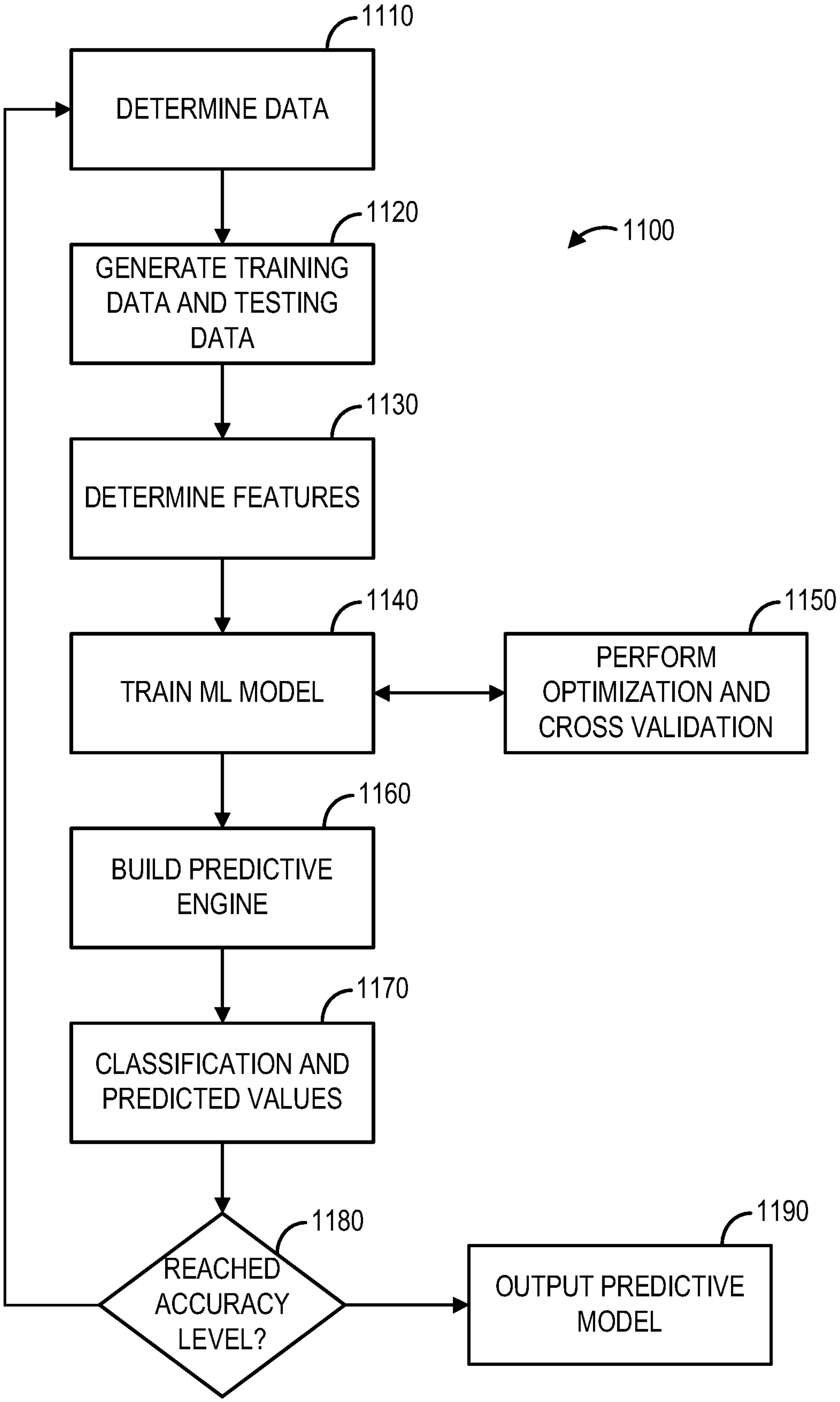
FIG. 11 shows an example method.

FIG. 11 is a flowchart illustrating an example training method 1100 for generating the ML module 930 using the training module 920. The training module 920 can implement supervised, unsupervised, and/or semi-supervised (e.g., reinforcement based) machine learning-based classification models 940. The method 1100 illustrated in FIG. 11 is an example of a supervised learning method; variations of this example of training method are discussed below, however, other training methods can be analogously implemented to train unsupervised and/or semi-supervised machine learning models.

The training method 1100 may determine (e.g., access, receive, retrieve, etc.) first sequence data at step 1110. The sequence data may comprise a labeled set of core promoter sequences and a labeled set of control sequences. The labels may correspond to promoter status (e.g., yes or no).

The training method 1100 may generate, at step 1120, a training data set and a testing data set. The training data set and the testing data set may be generated by randomly assigning labeled sequences to either the training data set or the testing data set. In some implementations, the assignment of labeled sequences as training or testing data may not be completely random. As an example, a majority of the labeled sequences may be used to generate the training data set. For example, 75% of the labeled sequences may be used to generate the training data set and 25% may be used to generate the testing data set. In another example, 80% of the labeled sequences may be used to generate the training data set and 20% may be used to generate the testing data set.

The training method 1100 may determine (e.g., extract, select, etc.), at step 1130, one or more features that can be used by, for example, a classifier to differentiate among different classification of promoter status (e.g., yes vs. no). As an example, the training method 1100 may determine a set features from the labeled sequences. In a further example, a set of features may be determined from labeled sequences different than the labeled sequences in either the training data set or the testing data set. In other words, labeled sequences may be used for feature determination, rather than for training a machine learning model. Such labeled sequences may be used to determine an initial set of features, which may be further reduced using the training data set. By way of example, the features described herein may comprise one or more sequence patterns, GC content, CpG content, known core promoter sequence motifs, ATG frequency, and/or relative entropy. For known core promoter sequence motif occurrences, the relative positioning with respect to the TSS may also be taken into account. Relative entropy is a measure of how similar a sequence is to a random sequence based on fixed nucleotide distributions (core promoter sequences are less random). Example probabilities for random DNA are: Probabilities for random DNA: A: 0.3, C: 0.2, T: 0.2, G: 0.3. FIG. 10 shows the relative significance of various features in predicting promoter status. For example, CpG dinucleotide content has the strongest positive correlation with core promoter identity. Random DNA has relatively few CpGs, whereas core promoters can have many (a subset of core promoters is called CpG islands). Presence or absence of a TATA box is also significant.

Returning to FIG. 11, the training method 1100 may train one or more machine learning models using the one or more features at step 1140. In one example, the machine learning models may be trained using supervised learning. In another example, other machine learning techniques may be employed, including unsupervised learning and semi-supervised. The machine learning models trained at 1140 may be selected based on different criteria depending on the problem to be solved and/or data available in the training data set. For example, machine learning classifiers can suffer from different degrees of bias. Accordingly, more than one machine learning model can be trained at 1140, optimized, improved, and cross-validated at step 1150.

The training method 1100 may select one or more machine learning models to build a predictive model at 1160. The predictive model may be evaluated using the testing data set. The predictive model may analyze the testing data set and generate predicted promoter statuses at step 1170. Predicted promoter statuses may be evaluated at step 1180 to determine whether such values have achieved a desired accuracy level. Performance of the predictive model may be evaluated in a number of ways based on a number of true positives, false positives, true negatives, and/or false negatives classifications of the plurality of data points indicated by the predictive model.

For example, the false positives of the predictive model may refer to a number of times the predictive model incorrectly classified a sequence as a promoter that was in reality not a promoter. Conversely, the false negatives of the predictive model may refer to a number of times the machine learning model classified a promoter sequence as not a promoter when, in fact, the sequence was a promoter. True negatives and true positives may refer to a number of times the predictive model correctly classified one or more sequences as a promoter or not a promoter. Related to these measurements are the concepts of recall and precision. Generally, recall refers to a ratio of true positives to a sum of true positives and false negatives, which quantifies a sensitivity of the predictive model. Similarly, precision refers to a ratio of true positives a sum of true and false positives. When such a desired accuracy level is reached, the training phase ends and the predictive model (e.g., the ML module 930) may be output at step 1190; when the desired accuracy level is not reached, however, then a subsequent iteration of the training method 1100 may be performed starting at step 1110 with variations such as, for example, considering a larger collection of sequence data.

2. Methods for Using the Predictive Model

Figure 12:
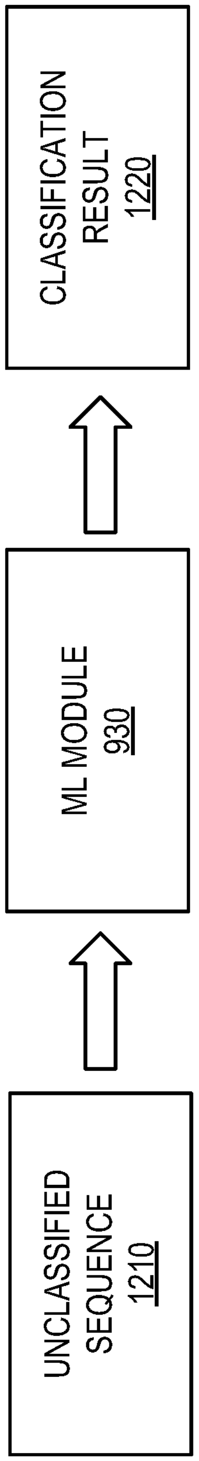
FIG. 12 shows an example method.

FIG. 12 is an illustration of an exemplary process flow for using a machine learning-based classifier to determine whether a nucleotide sequence is a promoter. As illustrated in FIG. 12, an unclassified sequence 1210 may be provided as input to the ML module 930. The ML module 930 may process the unclassified sequence 1210 using a machine learning-based classifier(s) to arrive at a classification result 1220.

The classification result 1220 may identify one or more characteristics of the unclassified sequence 1210. For example, the classification result 1220 may identify the promoter status of the unclassified sequence 1210 (e.g., whether or not the unclassified sequence 1210 is likely to perform a promoter function).

The ML module 930 may be used to classify a sequence generated by the generative model (e.g., the LSTM-RNN 710). The predictive model (e.g., the ML module 930) may serve as a quality control mechanism for the generative model (e.g., the LSTM-RNN 710). Before a sequence generated by the generative model is tested in an experimental setting, the predictive model may be used to test if the generated sequence would be predicted to be positive for core promoter activity.

F. Methods of Use

In some aspects, a specific promoter sequence is generated and/or identified by one or more of the methods described herein. Once a promoter sequence is identified, the promoter can be produced or engineered. In some aspects, the terms produced, engineered, and synthesized can be used interchangeably. In some aspects, a promoter can be chemically synthesized according to techniques in common use. See, for example, Beaucage et al. (1981) Tet. Lett. 22: 1859 and U.S. Pat. No. 4,668,777, herein incorporated by reference in their entirety. Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA. A promoter can also be synthesized using any of the techniques described in the patents disclosed in Yu et al. Recent Pat DNA Gene Seq, 2012, April; 6(1):10-21, each of which are incorporated by reference in their entireties.

Once a promoter has been produced, the promoter can be inserted in a nucleic acid construct. In some aspects, a nucleic acid construct can be a plasmid, including, but not limited to, plasmids used to produce viral vectors. In some aspects, a promoter can be inserted upstream of a transgene (i.e. gene of interest) that is already present in a plasmid used for making a virus. In some aspects, a promoter sequence can be inserted upstream of a transgene forming a nucleic acid sequence and then the nucleic acid sequence can be inserted into a plasmid used for making a virus. In some aspects, a promoter can be inserted into a plasmid prior to inserting the transgene. Any known cloning methods can be used to produce a plasmid or nucleic acid sequence comprising a promoter. For example, in some aspects, a plasmid used in producing a viral vector, such as an AAV, can be cut with one or more restriction endonucleases. A nucleic acid sequence comprising restriction endonuclease sites on the 5' and 3' ends with a specific promoter in between can be cut with the restriction endonucleases specific to the restriction endonuclease sites. In some aspects, the nucleic acid sequence comprising restriction endonuclease sites on the 5' and 3' ends with a specific promoter in between further comprises a transgene downstream of the promoter and is also in between the restriction endonuclease sites. In some aspects, the restriction endonuclease used to cut the plasmid is the same as the restriction endonuclease used to cut the nucleic acid sequence comprising restriction endonuclease sites on the 5' and 3' ends with a specific promoter in between. Cutting with the same restriction endonuclease(s) produces cohesive ends in the plasmid and the nucleic acid sequence comprising restriction endonuclease sites on the 5' and 3' ends and a specific promoter in between. In some aspects, a nucleic acid sequence comprising a specific promoter can be chemically synthesized to already contain specific restriction endonuclease sites at the ends that are already cohesive to a plasmid cut with restriction endonucleases therefore eliminating the step of cutting the nucleic acid sequence with the restriction endonuclease. Ultimately, a nucleic acid sequence and a plasmid having similar cohesive ends can be brought into contact with each other allowing for formation of a circular plasmid comprising a specific promoter upstream of a transgene. The circular plasmid can then be used to produce a virus, such as AAV, using known methods for virus production.

G. Examples

The following examples illustrate the present methods and systems. The following Examples are not intended to be limiting thereof.

Figure 13:
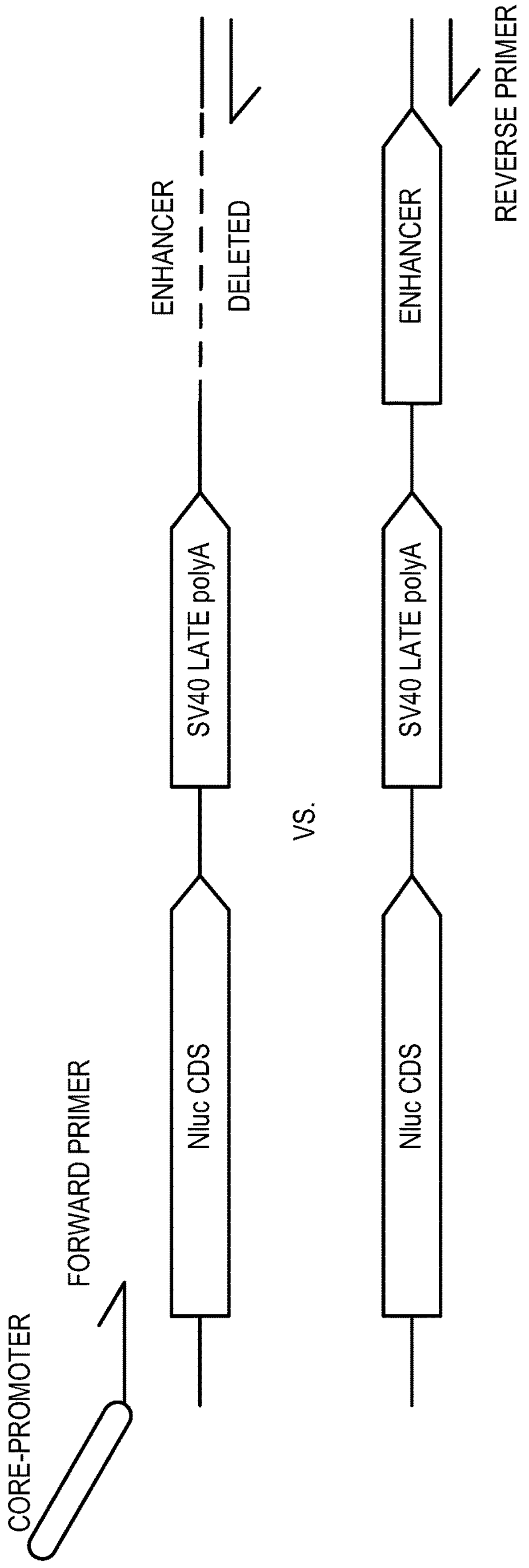
FIG. 13 shows an example promoter assay.

After identifying a core promoter sequence using the methods disclosed herein, the core promoter activity can be tested using a biological system. FIG. 13 is a schematic showing an overview of an example of how a promoter assay can be designed. To test individual core promoter (CP) candidates (controls or generated core promoters), two reporter constructs were designed. The reporter constructs contain the coding sequence of NanoLuc luciferase (Niue, Promega), a SV40 late polyadenylation signal and either a liver specific enhancer (from Kheradpour et al. or the enhancer omitted, followed by a universal reverse primer binding site. Additionally, a primer binding site was introduced upstream of the NanoLuc coding sequence in order to add the corepromoter candidate during PCR. The activating enhancer can be placed downstream of the reporter gene, to ensure that there is no transcription initiation within the enhancer.

The reporter constructs were ordered as a double-stranded DNA sample (gBlock, IDT) and diluted to 10 ng/μl in water. In order to generate reporter constructs that can be introduced into cells to assay luciferase activity, these two templates were used as universal templates for PCR during which the respective core promoter candidate was introduced via the 5' oligonucleotide. To do so, we ordered oligonucleotides containing the core promoter sequence followed by the sequence corresponding to the 5' primer binding site of the reporter construct. The resulting dsDNA PCR product consists of the core promoter candidate, the Nluc CDS, the SV40 late polyA and either the enhancer (FIG. 13 bottom) or no enhancer as a background control (FIG. 13 top). This linear dsDNA product can directly be used for transfection into a cell line of choice in order to assess luciferase activity. For PCR, we used 25 μl 2×Q5 hotstart mastermix (NEB), 2.5 μl forward oligo, 2.5 μl reverse oligo, 1 ng of gFM15 template 20 μl of $H_2O$. This reaction mix was amplified with the following PCR program: 98° C. for 30 s, 98° C. for 10 s, 68° C. for 30 s, 72° C. for 15 s, go to step 2 for 24 more times, 72° C. for 2 min, hold at 4° C. Finally, the PCR reaction was purified using Ampure XP beads (Beckman Coulter) using a 0.55 bead to PCR reaction ratio. Testing the core promoter candidates within the context of a PCR product, instead of on a plasmid ensures that there are no other confounding sequences present.

Figure 14:
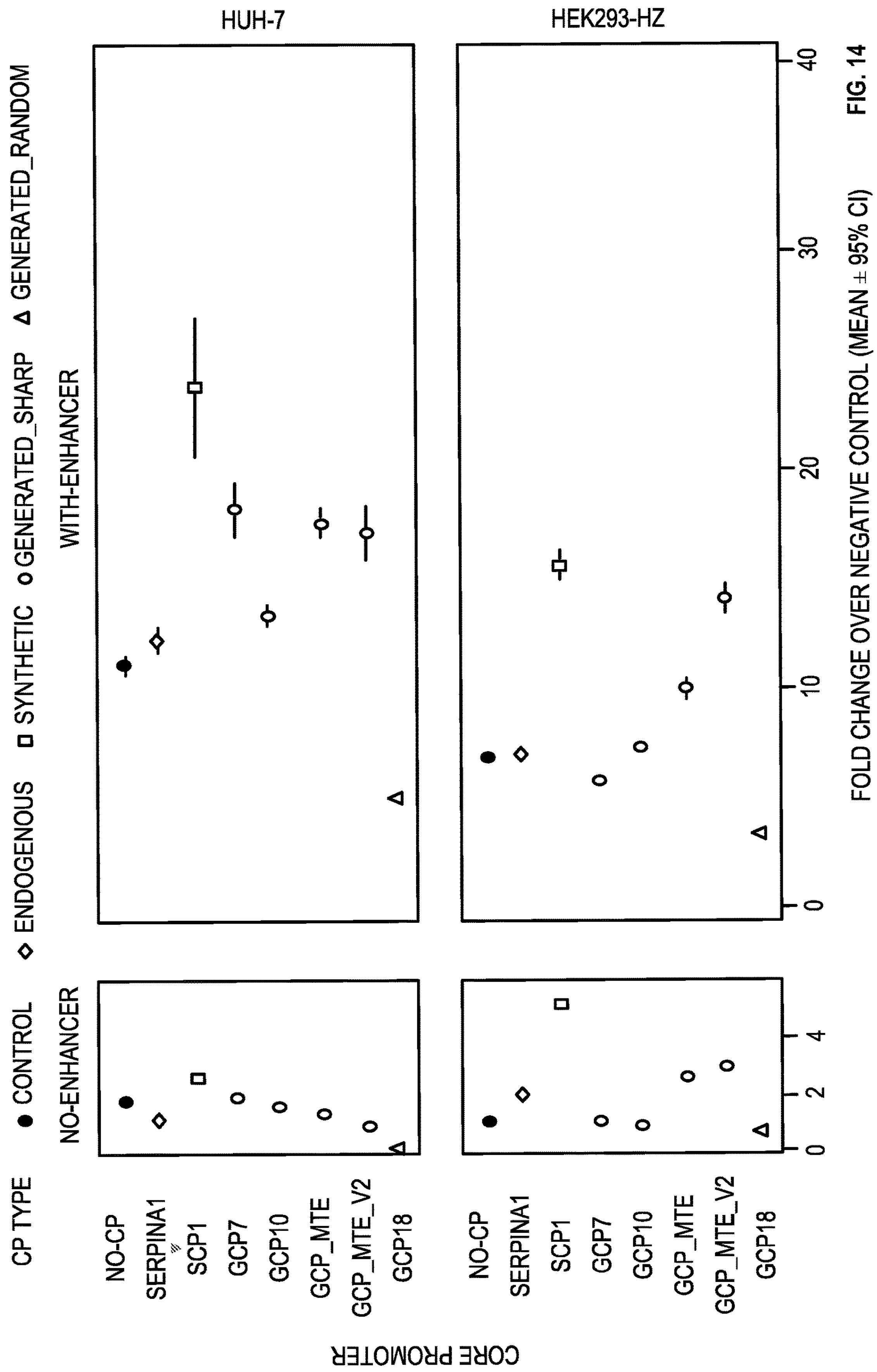
FIG. 14 shows a comparison of performance of generated core promoters to control core promoters.

FIG. 14 shows an in vitro promoter assay comparing generated core promoters (sequences shown in Table 1) to control core promoters. As shown in FIG. 14, "no-CP" is a control; "SerpinA1" is an endogenous core promoter; "SCP1" is a synthetic core promoter; "GCP7," "GCP10," "GCP_MTE," and "GCP_MTE_V2," are sharp core promoters generated according to the disclosed methods; and "GCP18" is a random core promoter generated according to the disclosed methods. Shown are fold change values (mean±95% confidence interval, CI) for generated core-promoters (CPs) and controls. All datapoints are normalized to the mean of the no-core promoter control without enhancer. Core promoters are grouped by type: control is the negative control without core promoter; endogenous is the core promoter of the liver expressed SerpinA1 gene; synthetic is an engineered core promoter such as SCP1 (Kadonaga lab); generated_sharp are generated core promoters based on a model trained on endogenous sharp core promoters; generated_random is a core promoter based on a model trained on endogenous random sequences (serves as an additional negative control). The left two panels depict fold-changes derived from reporter constructs without enhancer (baseline), the right two panels depict fold-changes derived from reporter constructs with enhancer (an endogenous liver enhancer for Huh-7, a minimal SFFV enhancer for HEK293-HZ). The top two panels are data obtained from Huh-7 cells; the lower two panels are data obtained from experiments done in HEK293 cells.

TABLE 1

The sequences of the generated core promoters.

| ID | SEQUENCE | SEQ ID NO: |
|---|---|---|
| SERPINA1 | CGTTGCCCCTCTGGATCCACTGCTTAAATACGGA CGAGGACAGGGCCCTGTCTCCTCAGCTTCAGGCA CCACCACTGACCTGGGACAGTGAA | 6 |
| SCP1 | CCCTAGGGTACTTATATAAGGGGGTGGGGGCGCG TTCGTCCTCAGTCGCGATCGAACACTCGAGCCGA GCAGACGTGCCTACGGACCGG | 7 |
| GCP7 | AGCTGAAACCAACTCTTGAGCAATATAAAAGCTG CTGCCCGGGACCCAGCGCAGAGCGGCGGCGGCGG CGGCGGCGGCGGCGGCGGCGGCGGCGCAGCGCT | 8 |
| GCP10 | CGCCGTGGCTATAAAAGCACTGCACACCCCGCCA ACCCAAACCCCGGCAA | 9 |
| GCP_MTE | GGGAACTGGTATAAAAGGGCCGGCGCTGGTTACC CAGTCCTTGGCGCCCCCTCGAGCCGAGCAGACGT GTCTAGTAGATCTCAC | 10 |
| GCP_MTE_V2 | GGGAACTGGTATAAAAGGGCCGGCGCTCGTGGCG TTACCCAGTCCTTGGCGCCCCCTCGAGCCGAGCA GACGTGTCTAGTAGATCTCAC | 11 |
| GCP18 | GTCTCTCCAGTTGGATCAGGTAGATAACTTTTTG AAACATTTTCTTATTGGGAAGATCTGGGTTCCAT TCTGCTCTCTGGGATTGCAGGTGTGAGCCACA | 12 |

The assay shown in FIG. 14 involves the transfection of Huh-7 and HEK293-HZ cells followed by luciferase assays. $1\times10^4$ Huh-7 or HEK293-HZ cells per well were plated in 96-well plates in DMEM+10% FBS, 24 h before being transfected with 0.1 g of reporter construct using Mirus TransIT-LT1 transfection reagent (Mirus Bio, #MIR 2304). As a transfection control, a firefly luciferase plasmid was co-transfected at a 1:9 ratio (Firefly plasmid: NanoLuc PCR product). To assay luciferase activity, the cells were lysed and processed 24 h after transfection using to the Nano-Glo dual-luciferase assay system (Promega, #N1610). Luciferase activity was measured using a SpectraMax i3 plate reader (Molecular Devices).

Computational Methods

Training Data

A list of candidate core promoters for the human genome was downloaded as transcriptional start site (TSS) profiling data from FANTOM5 (doi: 10.1038/sdata.2017.112) using the R package CAGEr (doi: 10.18129/B9.BIOC.CAGER) or direct download from $FANTOM_5$. From this data, two separate lists of core promoters were created for the predictive and generative model (see explanation of models below). For the generative model, the FANTOM5 datasets were filtered to only keep human, adult liver data (sample: liver__adult__pool1). The data was normalized (method="powerLaw", fitInRange=c(5, 1000), alpha=1.05, T=1*10^6), the TSSs were clustered and the interquantile width calculated (qLow=0.1, qUp=0.9). They were then binned into sharp and broad TSSs based on their interquantile width. Next, core promoter candidates were created by extending the TSS summit by 49 bp in the 5' and 50 bp in the 3' direction. Only the 2,950 strongest core promoters, based on their CAGE signal, were kept. As a control set, these core promoters were shifted by 50,000 bp in the 5' direction and those that after shifting overlapped with any CAGE peak were filtered out (n_control=2915).

For the predictive model, the top CAGE peaks of the entire FANTOM5 dataset (cutoff>50,000 in column 5 of hg19.cage_peak_phase1and2combined_coord.bed) were taken, then filtered out those that overlapped with any of the peaks for the generative model. Similarly to the peaks for the generative model, the TSS summits were extended by 49 bp in the 5' and 50 bp in the 3' direction to create the final list of core promoters. These core promoters were shifted by 50,000 bp in the 5' direction to create a list of negative control regions, which was further filtered against any CAGE peak or the negative control regions for the generative model. All of the above core promoter sequences were filtered against any sequence containing Ns in the human genome assembly (hg19). For the predictive model, each category of core promoters was saved as a sequence associated with a label (1=core promoter, 0=negative control).

Predictive Model

In order to train the predictive model, the labelled sequences were taken (see section on 'Training data') and features relevant to core promoter biology were extracted. GC content, AT and CG dinucleotide frequency, ATG frequency, core promoter motif occurrences and relative entropy were calculated (relative to a random sequence with 0.3, 0.2, 0.2, 0.3 frequencies for A, C, G, T, respectively). For motif occurrences, the relative positioning in respect to the TSS were also taken into account. Next, the training dataset was split into a training and validation set using train_test_split from scikit-learn (80% training, 20% validation, with label stratification; Scikit-learn: Machine Learning in Python, Pedregosa et al., JMLR 12, pp. 2825-2830, 2011, version 0.21.2). The above resulted in a training set of 11,339 examples and 2,835 validation examples with 19 features. A f1 weighted score as implemented in yellowbrick (doi: 10.5281/zenodo.3687330, version 0.9.1) was used to select hyper-parameters for a logistic regression model with L1 regularization: penalty='l1', solver='liblinear', multi_class='auto', C=0.5. All metrics such as the ROC and feature importance were visualized using yellowbrick.

Generative Model

In order to train the generative model, the core promoter sequences of the different classes were split into pairs of 10 nt seed sequences with the following nucleotide as the prediction target. To create the seed/target pairs, the core promoter sequences were split using a sliding window approach with a step size of 1. This resulted in 94,869 pairs for sharp CPs, 170,640 pairs for broad CPs and 261,720 pairs for random controls. These sequence pairs were vectorized using a simple numerical encoding ('A': 0, 'C': 1, 'G': 2, 'T': 3).

A long-short term memory (LSTM) recurrent neural network (RNN) was implemented using keras (2.2.4) with a TensorFlow backend (1.13.0-dev20190126). The LSTM had 128 units and was followed by a single, dense output layer with a softmax activation function. A RMSprop (lr=0.001) optimizer and categorical crossentropy was used as the loss function. This model was trained using the respective pairs (see above) as input with a batch size of 128 for 25 epochs, but early stopping was employed (monitoring loss, patience=1, min_delta=0.001). To generate new sequences, sampling from the learned probability distribution can be used to predict new nucleotides for a 'seed' sequence. The newly generated sequence can then be used as another seed for another cycle of sequence generation in an iterative process of sequence generation. To add stochasticity to this process, the originally learned probabilities were reweighed by a softmax temperature, before sampling from this newly derived distribution (temperature=0.8). Finally, this approach was used to generate novel core promoter sequences based on models trained using input from sharp, broad and random core promoter sequences. The length of these sequences ranged between 50 and 100 nt.

Figure 15:
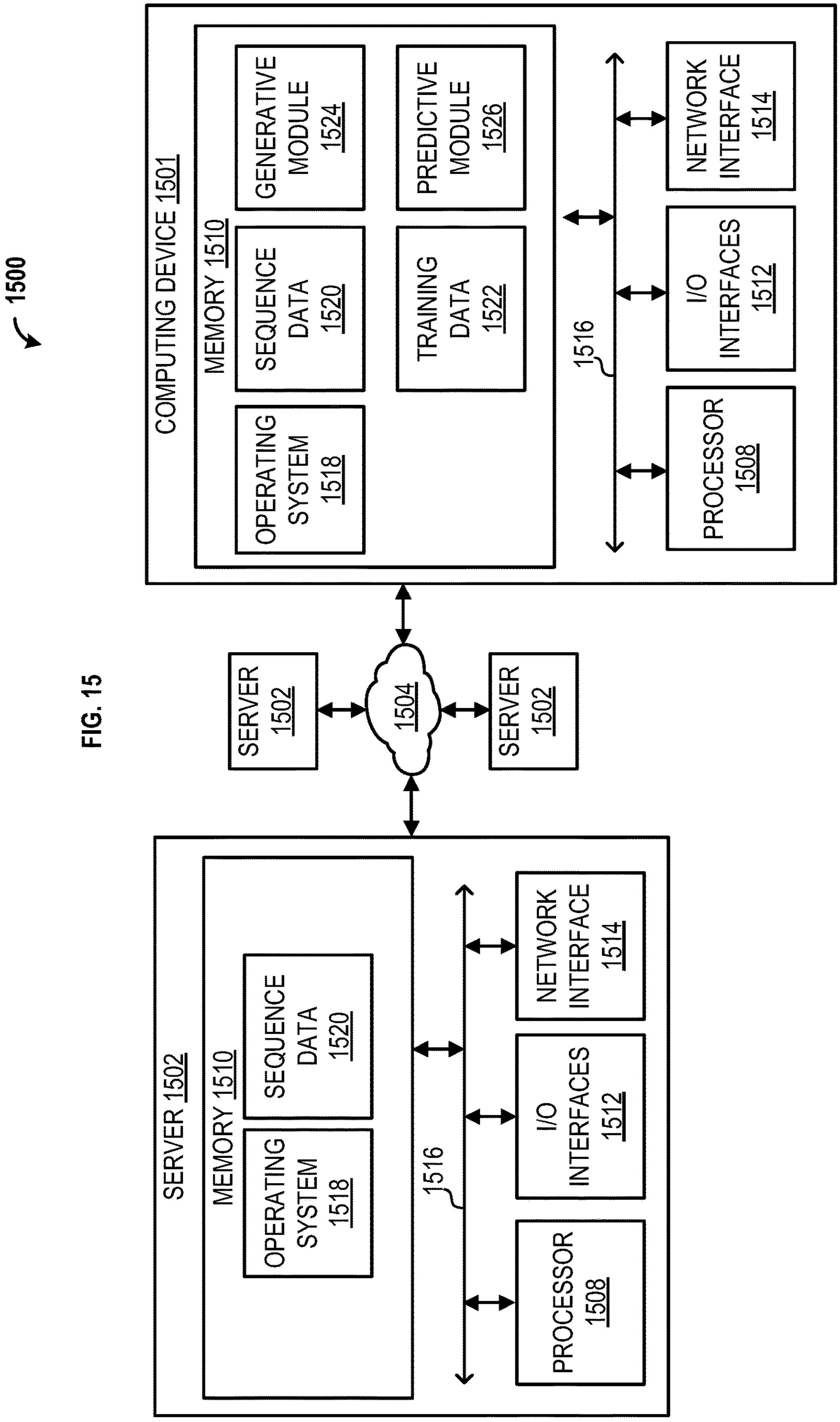
FIG. 15 shows an example operational environment.

FIG. 15 is a block diagram depicting an environment 1500 comprising non-limiting examples of a computing device 1501 and a server 1502 connected through a network 1504. In an aspect, some or all steps of any described method may be performed on a computing device as described herein. The computing device 1501 can comprise one or multiple computers configured to store one or more of sequence data 1520 (e.g., promoter sequence data, such as CAGE data), training data 1522 (e.g., labeled sequence data: core promoter sequences and control sequences), a generative module 1524 (e.g., the LSTM-RNN 710, including any ancillary training modules), a predictive module 1526 (e.g., the ML module 930, including any ancillary training modules), and the like. The server 1502 can comprise one or multiple computers configured to store the sequence data 1520. Multiple servers 1502 can communicate with the computing device 1501 via the through the network 1504. In an embodiment, the server 1502 may comprise a repository for data generated by a CAGE experiment.

The computing device 1501 and the server 1502 can be a digital computer that, in terms of hardware architecture, generally includes a processor 1508, memory system 1510, input/output (I/O) interfaces 1512, and network interfaces 1514. These components (1508, 1510, 1512, and 1514) are communicatively coupled via a local interface 1516. The local interface 1516 can be, for example, but not limited to, one or more buses or other wired or wireless connections, as is known in the art. The local interface 1516 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1508 can be a hardware device for executing software, particularly that stored in memory system 1510. The processor 1508 can be any custom made or commercially available processor, a central processing unit (CPU), an auxiliary processor among several processors associated with the computing device 1501 and the server 1502, a semiconductor-based microprocessor (in the form of a microchip or chip set), or generally any device for executing software instructions. When the computing device 1501 and/or the server 1502 is in operation, the processor 1508 can be configured to execute software stored within the memory system 1510, to communicate data to and from the memory system 1510, and to generally control operations of the computing device 1501 and the server 1502 pursuant to the software.

The I/O interfaces 1512 can be used to receive user input from, and/or for providing system output to, one or more devices or components. User input can be provided via, for example, a keyboard and/or a mouse. System output can be provided via a display device and a printer (not shown). I/O interfaces 1512 can include, for example, a serial port, a parallel port, a Small Computer System Interface (SCSI), an infrared (IR) interface, a radio frequency (RF) interface, and/or a universal serial bus (USB) interface.

The network interface 1514 can be used to transmit and receive from the computing device 1501 and/or the server 1502 on the network 1504. The network interface 1514 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi, cellular, satellite), or any other suitable network interface device. The network interface 1514 may include address, control, and/or data connections to enable appropriate communications on the network 1504.

The memory system 1510 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1510 may incorporate electronic, magnetic, optical, and/or other types of storage media. Note that the memory system 1510 can have a distributed architecture, where various components are situated remote from one another, but can be accessed by the processor 1508.

The software in memory system 1510 may include one or more software programs, each of which comprises an ordered listing of executable instructions for implementing logical functions. In the example of FIG. 15, the software in the memory system 1510 of the computing device 1501 can comprise the sequence data 1520, the training data 1522, the generative module 1524, the predictive module 1526, and a suitable operating system (O/S) 1518. In the example of FIG. 15, the software in the memory system 1510 of the server 1502 can comprise, the sequence data 1520, and a suitable operating system (O/S) 1518. The operating system 1518 essentially controls the execution of other computer programs and provides scheduling, input-output control, file and data management, memory management, and communication control and related services.

For purposes of illustration, application programs and other executable program components such as the operating system 1518 are illustrated herein as discrete blocks, although it is recognized that such programs and components can reside at various times in different storage components of the computing device 1501 and/or the server 1502. An implementation of the generative module 1524 and/or the predictive module 1526 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CDROM, digital versatile disks (DVD) or other optical storage, magnetic cassettes, magnetic tape, magnetic disk storage or other magnetic storage devices, or any other medium which can be used to store the desired information and which can be accessed by a computer.

Figure 16:
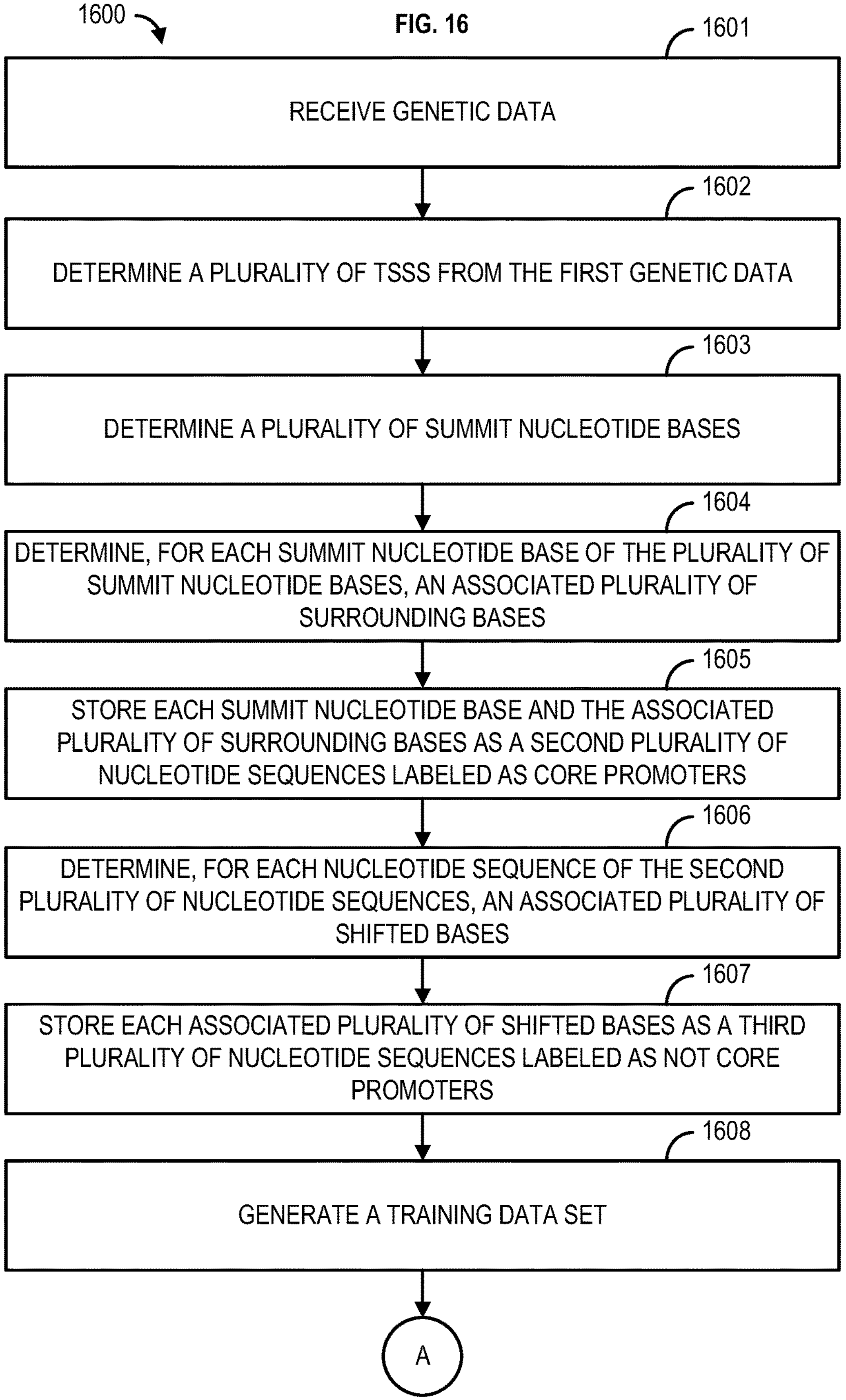
FIG. 16 shows an example method.
Figure 16:
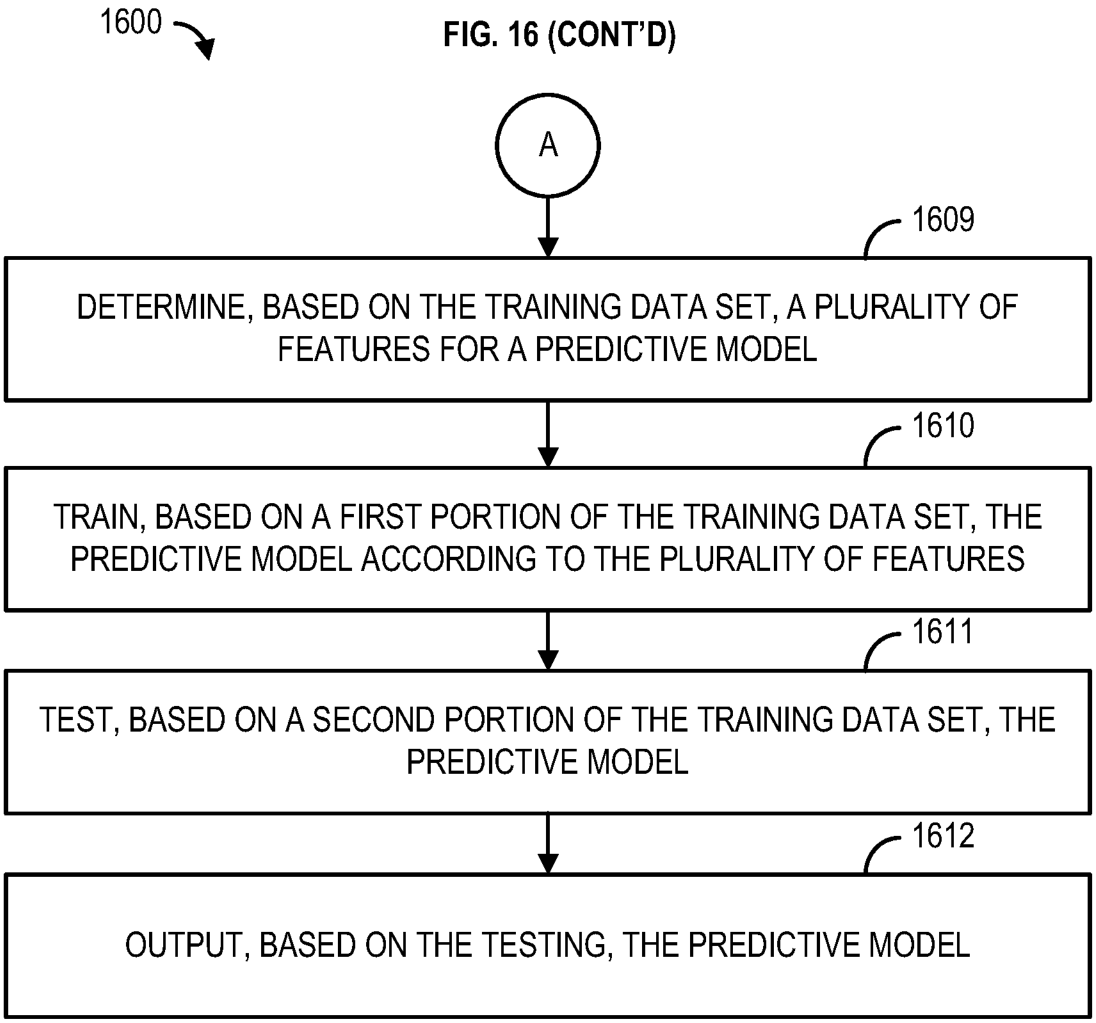

In an embodiment, the predictive module 1526 may be configured to perform a method 1600, shown in FIG. 16. The method 1600 may be performed in whole or in part by a single computing device, a plurality of electronic devices, and the like. The method 1600 may comprise receiving genetic data, wherein the genetic data comprises a first plurality of nucleotide sequences, wherein each nucleotide sequence of the plurality of nucleotide sequences comprises at least one transcription start site (TSS) having an associated expression score at 1601. The associated expression score may include a Cap Analysis of Gene Expression (CAGE) peak.

The method 1600 may comprise determining, based on the associated expression scores satisfying a threshold, a plurality of TSSs from the first plurality of nucleotide sequences at 1602.

The method 1600 may comprise determining, based on the plurality of TSSs, a plurality of summit nucleotide bases at 1603. Determining, based on the plurality of TSSs, the plurality of summit nucleotide bases may comprise determining, for each of the plurality of TSSs, a nucleotide base having a strongest CAGE signal.

The method 1600 may comprise determining, for each summit nucleotide base of the plurality of summit nucleotide bases, an associated plurality of surrounding bases at 1604. Determining, for each summit nucleotide base of the plurality of summit nucleotide bases, the associated plurality of surrounding bases may comprise determining, for each summit nucleotide base of the plurality of summit nucleotide bases, a first plurality of nucleotide bases in the 5' direction and a second plurality of nucleotide bases in the 3' direction. The first plurality of nucleotide bases in the 5' direction may comprise 49 nucleotide bases and the second plurality of nucleotide bases in the 3' direction may comprise 50 nucleotide bases.

The method 1600 may comprise storing each summit nucleotide base and the associated plurality of surrounding bases as a second plurality of nucleotide sequences labeled as core promoters at 1605.

The method 1600 may comprise determining, for each nucleotide sequence of the second plurality of nucleotide sequences, an associated plurality of shifted bases at 1606. Determining, for each nucleotide sequence of the second plurality of nucleotide sequences, the associated plurality of shifted bases may comprise shifting a quantity of nucleotide bases away from each nucleotide sequence of the second plurality of nucleotide sequences.

The method 1600 may comprise storing each associated plurality of shifted bases as a third plurality of nucleotide sequences labeled as not core promoters at 1607.

The method 1600 may comprise generating, based on the second plurality of nucleotide sequences labeled as core promoters and the third plurality of nucleotide sequences labeled as not core promoters, a training data set at 1608.

The method 1600 may comprise determining, based on the training data set, a plurality of features for a predictive model at 1609. The plurality of features for the predictive model may comprise one or more of GC content, AT and CG dinucleotide frequency, ATG frequency, core promoter motif occurrences, relative entropy, and relative positioning relative to an associated TSS.

At 1610, The method 1600 may comprise training, based on a first portion of the training data set, the predictive model according to the plurality of features at 1610.

The method 1600 may comprise testing, based on a second portion of the training data set, the predictive model at 1611.

The method 1600 may comprise outputting, based on the testing, the predictive model at 1612.

In an embodiment, the method 1600 may further comprise filtering out any TSS of the plurality of TSSs from the first plurality of nucleotide sequences having an expression score that overlaps with an expression score for a TSS used in a generative model. In an embodiment, the method 1600 may further comprise filtering out any nucleotide sequence of the second plurality of nucleotide sequences containing Ns in the human genome assembly (hg19).

Figure 17:
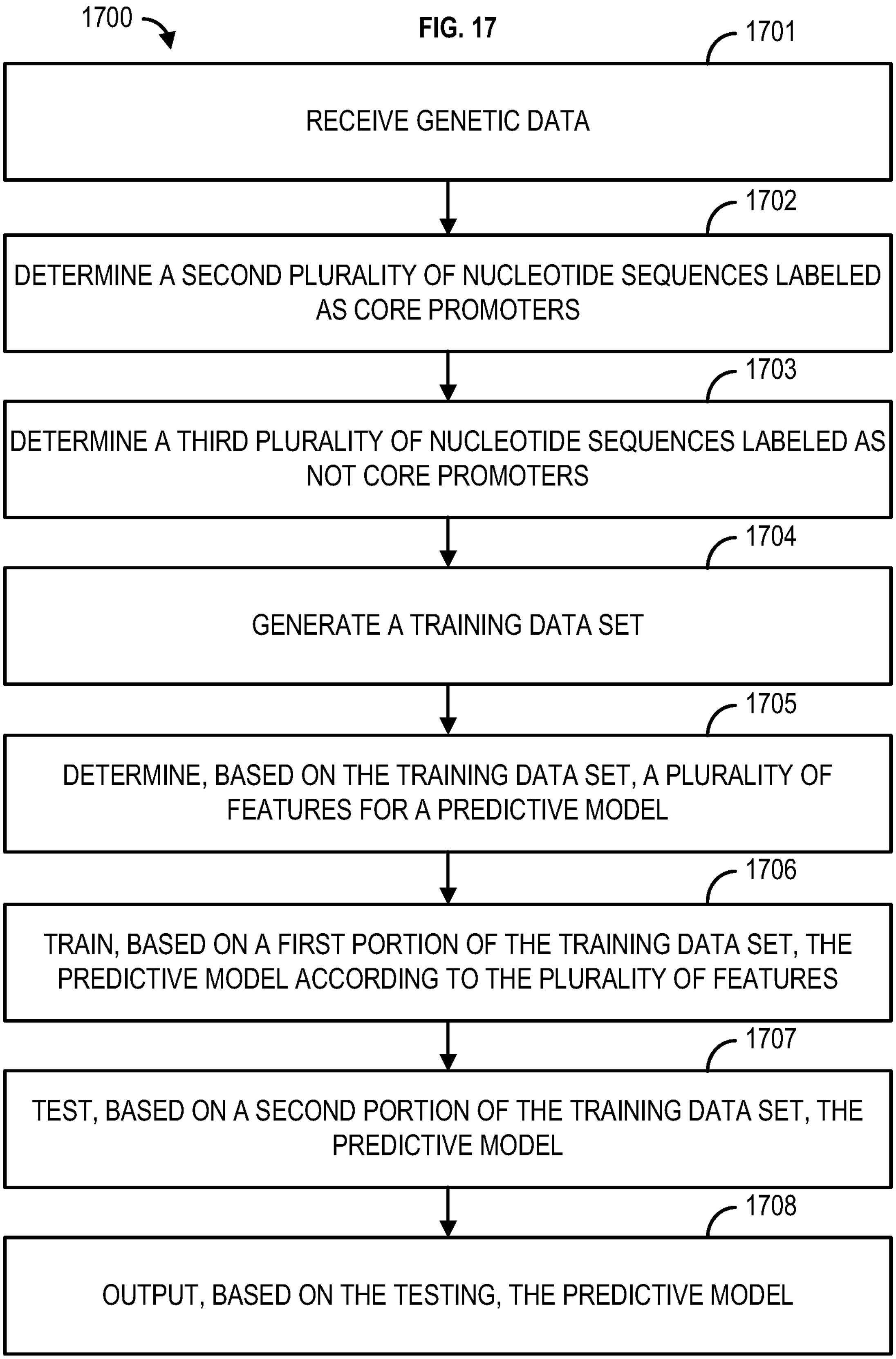
FIG. 17 shows an example method.

In an embodiment, the predictive module 1526 may be configured to perform a method 1700, shown in FIG. 17. The method 1700 may be performed in whole or in part by a single computing device, a plurality of electronic devices, and the like. The method 1700 may comprise receiving genetic data, wherein the genetic data comprises a first plurality of nucleotide sequences, wherein each nucleotide sequence of the plurality of nucleotide sequences comprises at least one transcription start site (TSS) having an associated expression score at 1701. The associated expression score may comprise a Cap Analysis of Gene Expression (CAGE) peak.

The method 1700 may comprise determining, based on the first plurality of nucleotide sequences, a second plurality of nucleotide sequences labeled as core promoters at 1702. Determining, based on the first plurality of nucleotide sequences, a second plurality of nucleotide sequences labeled as core promoters may comprise: determining, based on the associated expression scores satisfying a threshold, a plurality of TSSs from the first plurality of nucleotide sequences, determining, based on the plurality of TSSs, a plurality of summit nucleotide bases, determining, for each summit nucleotide base of the plurality of summit nucleotide bases, an associated plurality of surrounding bases, and storing each summit nucleotide base and the associated plurality of surrounding bases as the second plurality of nucleotide sequences labeled as core promoters.

Determining, based on the plurality of TSSs, the plurality of summit nucleotide bases may include determining, for each of the plurality of TSSs, a nucleotide base having a strongest CAGE signal. Determining, for each summit nucleotide base of the plurality of summit nucleotide bases, the associated plurality of surrounding bases may comprise determining, for each summit nucleotide base of the plurality of summit nucleotide bases, a first plurality of nucleotide bases in the 5' direction and a second plurality of nucleotide bases in the 3' direction. The first plurality of nucleotide bases in the 5' direction may comprise 49 nucleotide bases and the second plurality of nucleotide bases in the 3' direction comprises 50 nucleotide bases.

The method 1700 may comprise determining, based on the second plurality of nucleotide sequences, a third plurality of nucleotide sequences labeled as not core promoters at 1703. Determining, based on the second plurality of nucleotide sequences, a third plurality of nucleotide sequences labeled as not core promoters may comprise: determining, for each nucleotide sequence of the second plurality of nucleotide sequences, an associated plurality of shifted bases, and storing each associated plurality of shifted bases as a third plurality of nucleotide sequences labeled as not core promoters.

Determining, for each nucleotide sequence of the second plurality of nucleotide sequences, the associated plurality of shifted bases may comprise shifting a quantity of nucleotide bases away from each nucleotide sequence of the second plurality of nucleotide sequences.

The method 1700 may comprise generating, based on the second plurality of nucleotide sequences labeled as core promoters and the third plurality of nucleotide sequences labeled as not core promoters, a training data set at 1704.

The method 1700 may comprise determining, based on the training data set, a plurality of features for a predictive model at 1705. The plurality of features for the predictive model may comprise one or more of GC content, AT and CG dinucleotide frequency, ATG frequency, core promoter motif occurrences, relative entropy, and relative positioning relative to an associated TSS.

The method 1700 may comprise training, based on a first portion of the training data set, the predictive model according to the plurality of features at 1706.

The method 1700 may comprise testing, based on a second portion of the training data set, the predictive model at 1707.

The method 1700 may comprise outputting, based on the testing, the predictive model at 1708.

In an embodiment, the method of clam 1700 may also comprise filtering out any TSS of the plurality of TSSs from the first plurality of nucleotide sequences having an expression score that overlaps with an expression score for a TSS used in a generative model. In an embodiment, the method 1700 may further comprise filtering out any nucleotide sequence of the second plurality of nucleotide sequences containing Ns in the human genome assembly (hg19).

Figure 18:
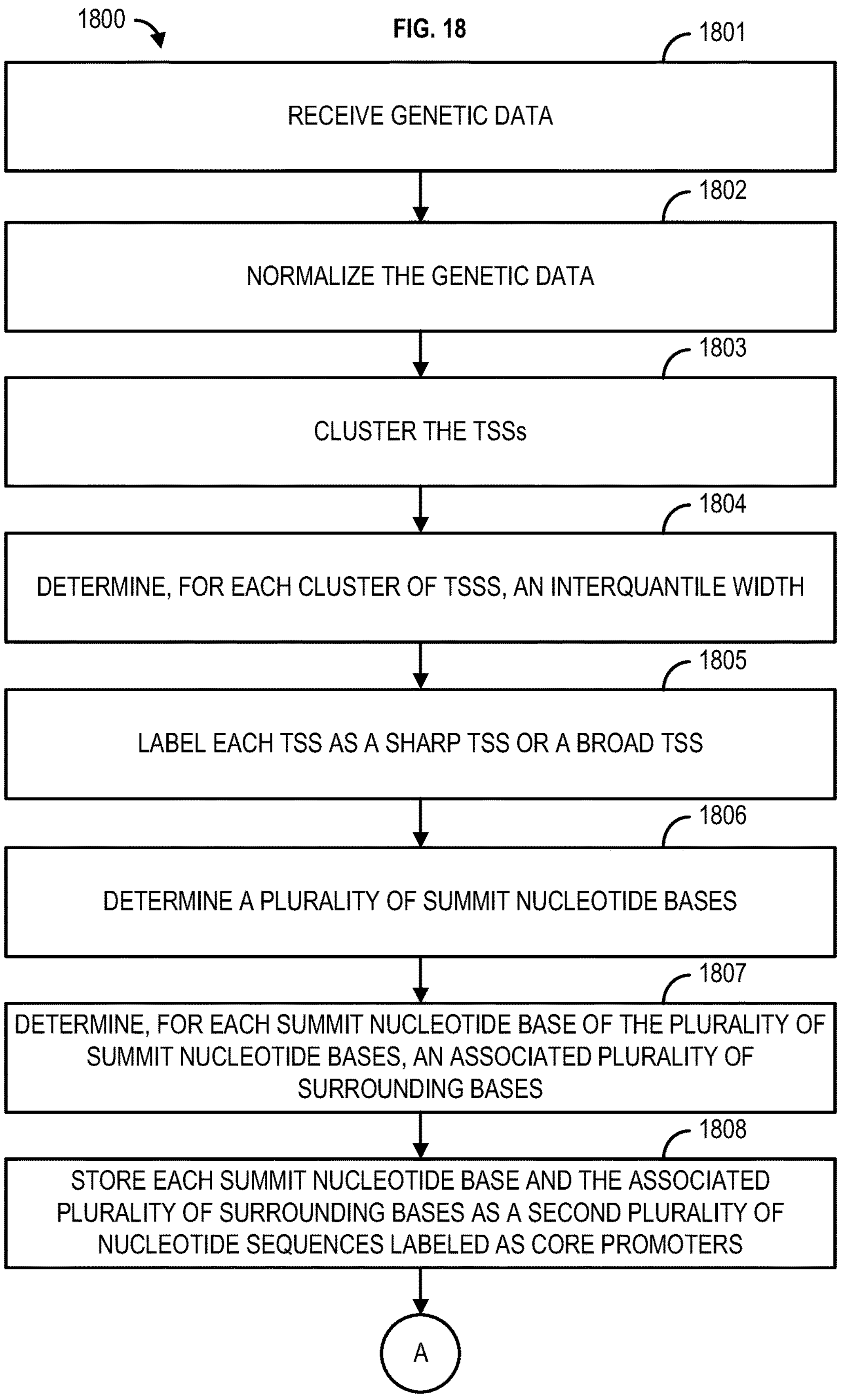
FIG. 18 shows an example method.
Figure 18:
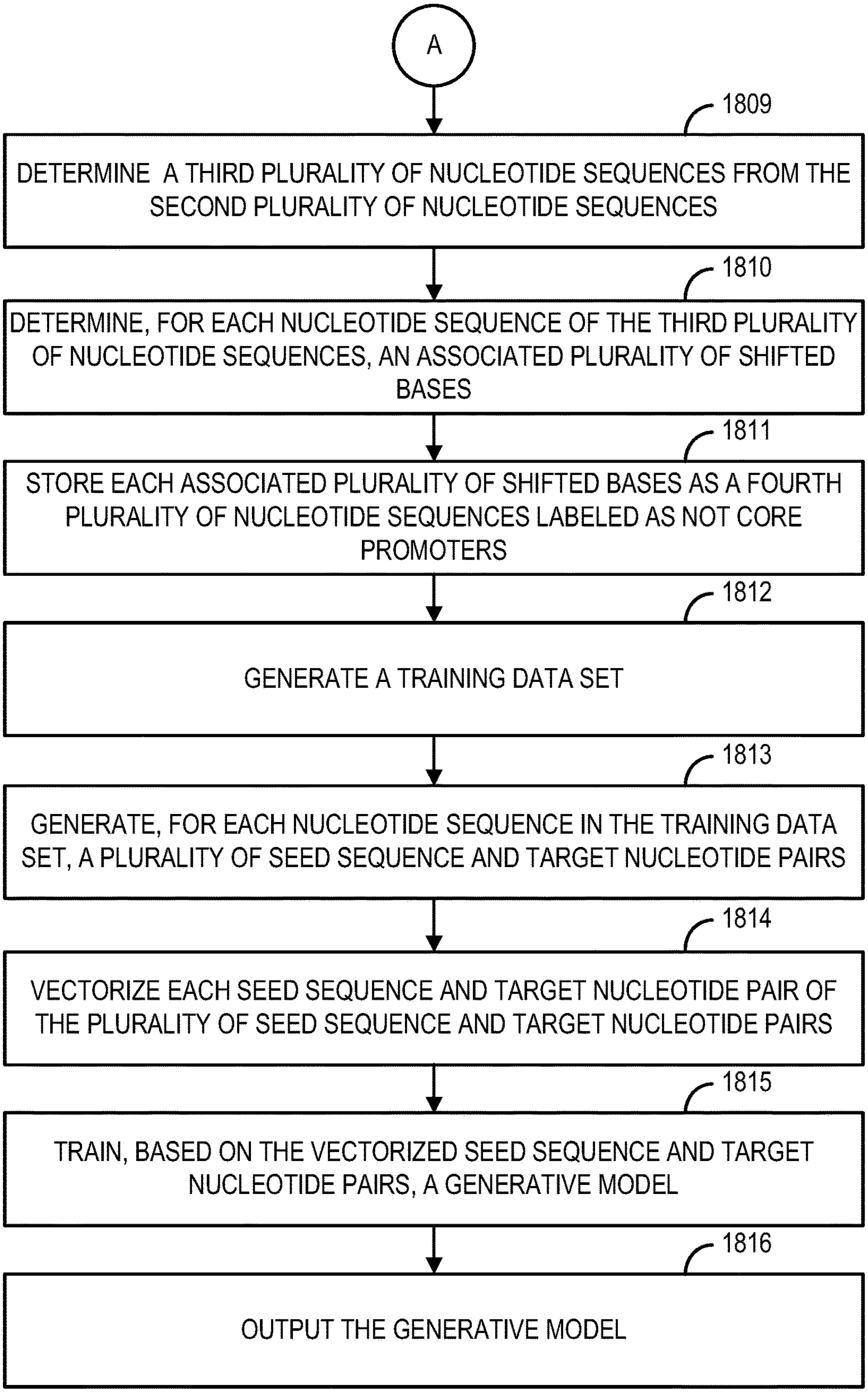

In an embodiment, the generative module 1524 may be configured to perform a method 1800, shown in FIG. 18. The method 1800 may be performed in whole or in part by a single computing device, a plurality of electronic devices, and the like. The method 1800 may comprise receiving genetic data, wherein the genetic data comprises a first plurality of nucleotide sequences, wherein each nucleotide sequence of the plurality of nucleotide sequences comprises at least one transcription start site (TSS) having an associated expression score at 1801. The associated expression score may comprise a Cap Analysis of Gene Expression (CAGE) peak.

The method 1800 may comprise normalizing the genetic data at 1802.

The method 1800 may comprise clustering, based on the associated expression scores, the TSSs at 1803.

The method 1800 may comprise determining, for each cluster of TSSs, an interquantile width at 1804.

The method 1800 may comprise labeling, based on the interquantile width, each TSS as a sharp TSS or a broad TSS at 1805.

The method 1800 may comprise determining, based on the plurality of TSSs, a plurality of summit nucleotide bases at 1806. Determining, based on the plurality of TSSs, the plurality of summit nucleotide bases may comprise determining, for each of the plurality of TSSs, a nucleotide base having a strongest CAGE signal.

The method 1800 may comprise determining, for each summit nucleotide base of the plurality of summit nucleotide bases, an associated plurality of surrounding bases at 1807. Determining, for each summit nucleotide base of the plurality of summit nucleotide bases, the associated plurality of surrounding bases may comprise determining, for each summit nucleotide base of the plurality of summit nucleotide bases, a first plurality of nucleotide bases in the 5' direction and a second plurality of nucleotide bases in the 3' direction. The first plurality of nucleotide bases in the 5' direction comprises 49 nucleotide bases and the second plurality of nucleotide bases in the 3' direction comprises 50 nucleotide bases.

The method 1800 may comprise storing each summit nucleotide base and the associated plurality of surrounding bases as a second plurality of nucleotide sequences labeled as core promoters at 1808.

The method 1800 may comprise determining, based on the associated expression scores satisfying a threshold, a third plurality of nucleotide sequences from the second plurality of nucleotide sequences at 1809.

The method 1800 may comprise determining, for each nucleotide sequence of the third plurality of nucleotide sequences, an associated plurality of shifted bases at 1810. Determining, for each nucleotide sequence of the third plurality of nucleotide sequences, the associated plurality of shifted bases may comprise shifting a quantity of nucleotide bases away from each nucleotide sequence of the third plurality of nucleotide sequences.

The method 1800 may comprise storing each associated plurality of shifted bases as a fourth plurality of nucleotide sequences labeled as not core promoters at 1811.

The method 1800 may comprise generating, based on the third plurality of nucleotide sequences labeled as core promoters and the fourth plurality of nucleotide sequences labeled as not core promoters, a training data set at 1812.

The method 1800 may comprise generating, for each nucleotide sequence in the training data set, a plurality of seed sequence and target nucleotide pairs at 1813. Generating, for each nucleotide sequence in the training data set, the plurality of seed sequence and target nucleotide pairs may comprise: dividing, based on sharp TSS or broad TSS labeling, the nucleotide sequences in the training data set into a sharp TSS group or a broad TSS group, applying a sliding window of the defined length and having a defined step size to each nucleotide sequence, and storing, at each step of the sliding window, a seed sequence and target nucleotide pair.

The method 1800 may comprise vectorizing each seed sequence and target nucleotide pair of the plurality of seed sequence and target nucleotide pairs at 1814. Each seed sequence and target nucleotide pair may comprise a seed sequence having a defined length and a target nucleotide immediately following the seed sequence on a given nucleotide sequence. The defined length may be, for example, 10 bases. Vectorizing each seed sequence and target nucleotide pair of the plurality of seed sequence and target nucleotide pairs may comprise encoding each nucleotide as a respective number.

The method 1800 may comprise training, based on the vectorized seed sequence and target nucleotide pairs, a generative model at 1815. The generative model may comprise a long-short term memory (LSTM) recurrent neural network (RNN).

The method 1800 may comprise outputting the generative model at 1816.

In an embodiment the method 1800 may comprise filtering out any nucleotide sequence of the second plurality of nucleotide sequences containing Ns in the human genome assembly (hg19).

In an embodiment, the method 1800 may comprise generating, based on the generative model, a nucleotide sequence. The nucleotide sequence may be, for example, a core promoter sequence. The method 1800 may comprise engineering a promoter based on the core promoter sequence.

Generating, based on the generative model, the nucleotide sequence may comprise: (a) receiving a seed sequence, (b) predicting, based on the seed sequence, a next nucleotide. (c) appending the next nucleotide to the seed sequence, and (d) repeating b-c until a desired length for the nucleotide sequence is reached. The desired length may be, for example, from about 50 nucleotides to about 100 nucleotides.

In an embodiment, the method 1800 may comprise inserting the promoter into a nucleic acid construct. Inserting the promoter into the nucleic acid construct may comprise inserting the promoter into the nucleic acid construct upstream of a transgene to drive expression of the transgene.

In an embodiment, the method 1800 may comprise producing an adeno associated virus or a lentivirus comprising the nucleic acid construct.

Figure 19:
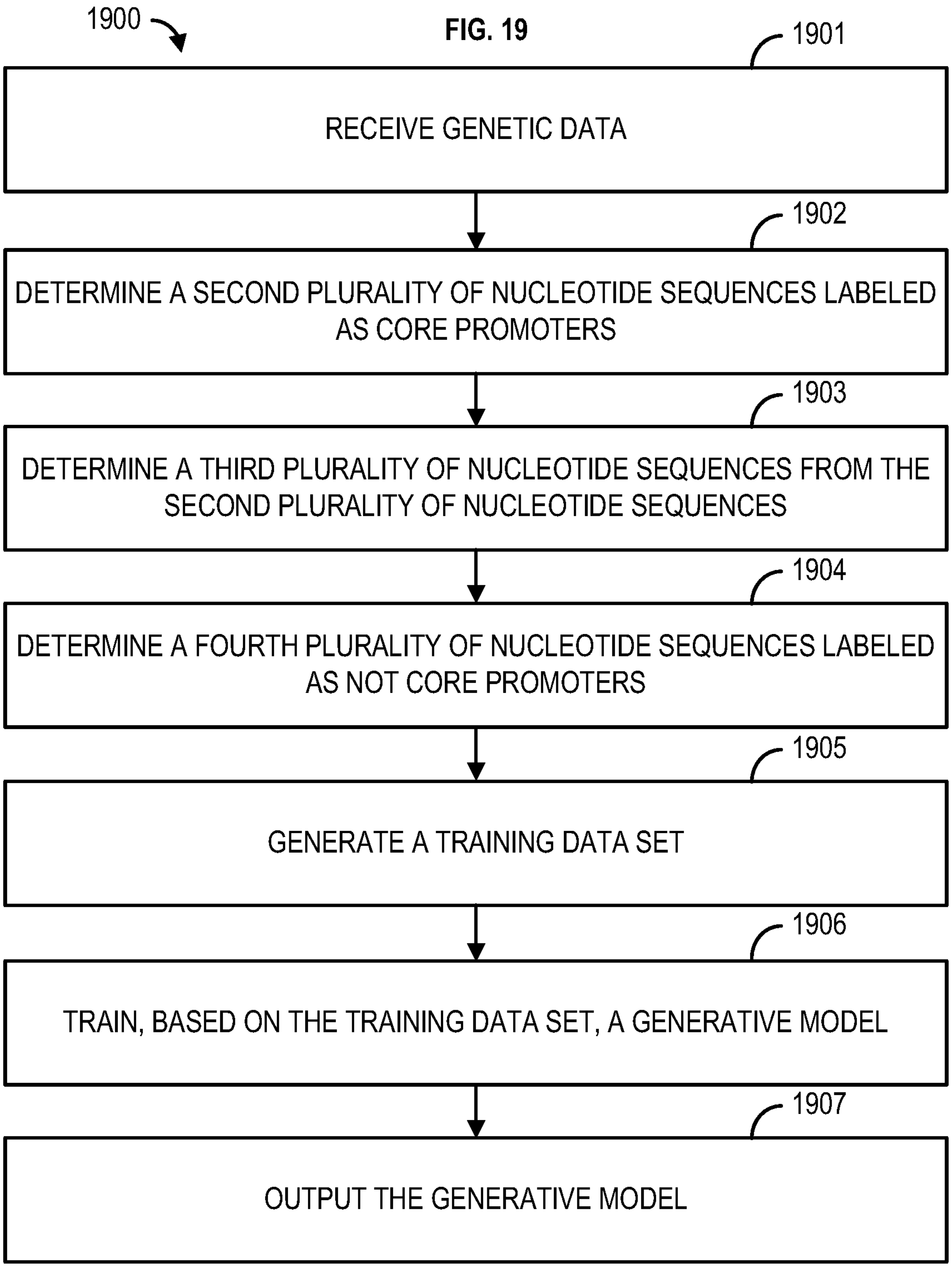
FIG. 19 shows an example method.

In an embodiment, the generative module 1524 may be configured to perform a method 1900, shown in FIG. 19. The method 1900 may be performed in whole or in part by a single computing device, a plurality of electronic devices, and the like. The method 1900 may comprise receiving genetic data, wherein the genetic data comprises a first plurality of nucleotide sequences, wherein each nucleotide sequence of the plurality of nucleotide sequences comprises at least one transcription start site (TSS) having an associated expression score at 1901. The associated expression score may comprise a Cap Analysis of Gene Expression (CAGE) peak.

The method 1900 may comprise determining, based on the first plurality of nucleotide sequences, a second plurality of nucleotide sequences labeled as core promoters at 1902. Determining, based on the first plurality of nucleotide sequences, the second plurality of nucleotide sequences labeled as core promoters may comprise: determining, based on the plurality of TSSs, a plurality of summit nucleotide bases, determining, for each summit nucleotide base of the plurality of summit nucleotide bases, an associated plurality of surrounding bases, and storing each summit nucleotide base and the associated plurality of surrounding bases as the second plurality of nucleotide sequences labeled as core promoters.

Determining, based on the plurality of TSSs, the plurality of summit nucleotide bases comprises determining, for each of the plurality of TSSs, a nucleotide base having a strongest CAGE signal. Determining, for each summit nucleotide base of the plurality of summit nucleotide bases, the associated plurality of surrounding bases may comprise determining, for each summit nucleotide base of the plurality of summit nucleotide bases, a first plurality of nucleotide bases in the 5' direction and a second plurality of nucleotide bases in the 3' direction. The first plurality of nucleotide bases in the 5' direction may comprise 49 nucleotide bases and the second plurality of nucleotide bases in the 3' direction may comprise 50 nucleotide bases.

The method 1900 may comprise determining, based on the associated expression scores satisfying a threshold, a third plurality of nucleotide sequences from the second plurality of nucleotide sequences at 1903.

The method 1900 may comprise determining, based on the third plurality of nucleotide sequences, a fourth plurality of nucleotide sequences labeled as not core promoters at 1904. Determining, based on the third plurality of nucleotide sequences, the fourth plurality of nucleotide sequences labeled as not core promoters may comprise: determining, for each nucleotide sequence of the third plurality of nucleotide sequences, an associated plurality of shifted bases, and storing each associated plurality of shifted bases as a fourth plurality of nucleotide sequences labeled as not core promoters.

Determining, for each nucleotide sequence of the third plurality of nucleotide sequences, the associated plurality of shifted bases may comprise shifting a quantity of nucleotide bases away from each nucleotide sequence of the third plurality of nucleotide sequences.

The method 1900 may comprise generating, based on the third plurality of nucleotide sequences labeled as core promoters and the fourth plurality of nucleotide sequences labeled as not core promoters, a training data set at 1905.

The method 1900 may comprise training, based on the training data set, a generative model at 1906. The generative model may comprise, for example, a long-short term memory (LSTM) recurrent neural network (RNN). Training, based on the training data set, the generative model may comprise: generating, for each nucleotide sequence in the training data set, a plurality of seed sequence and target nucleotide pairs, vectorizing each seed sequence and target nucleotide pair of the plurality of seed sequence and target nucleotide pairs, and training, based on the vectorized seed sequence and target nucleotide pairs, the generative model.

Each seed sequence and target nucleotide pair may comprise a seed sequence having a defined length and a target nucleotide immediately following the seed sequence on a given nucleotide sequence. The defined length may be, for example, 10 bases. Vectorizing each seed sequence and target nucleotide pair of the plurality of seed sequence and target nucleotide pairs may comprise encoding each nucleotide as a respective number.

The method 1900 may comprise outputting the generative model at 1907.

In an embodiment, the method 1900 may comprise normalizing the genetic data. In an embodiment, the method 1900 may comprise clustering, based on the associated expression scores, the TSSs, determining, for each cluster of TSSs, an interquantile width, and labeling, based on the interquantile width, each TSS as a sharp TSS or a broad TSS.

In an embodiment, the method 1900 may comprise generating, based on the generative model, a nucleotide sequence. The nucleotide sequence may be, for example, a core promoter sequence.

In an embodiment, the method 1900 may comprise engineering a promoter based on the core promoter sequence. The method 1900 may comprise inserting the promoter into a nucleic acid construct. Inserting the promoter into the nucleic acid construct may comprise inserting the promoter into the nucleic acid construct upstream of a transgene to drive expression of the transgene.

In an embodiment, the method 1900 may comprise producing an adeno associated virus or a lenti-virus comprising the nucleic acid construct.

In an embodiment the method 1900 may comprise filtering out any nucleotide sequence of the second plurality of nucleotide sequences containing Ns in the human genome assembly (hg19).

In an embodiment, the method 1900 may comprise generating, based on the generative model, a nucleotide sequence. The nucleotide sequence may be, for example, a core promoter sequence. The method 1900 may comprise engineering a promoter based on the core promoter sequence.

Generating, based on the generative model, the nucleotide sequence may comprise: (a) receiving a seed sequence, (b) predicting, based on the seed sequence, a next nucleotide. (c) appending the next nucleotide to the seed sequence, and (d) repeating b-c until a desired length for the nucleotide sequence is reached. The desired length may be, for example, from about 50 nucleotides to about 100 nucleotides.

In an embodiment, the method 1900 may comprise inserting the promoter into a nucleic acid construct. Inserting the promoter into the nucleic acid construct may comprise inserting the promoter into the nucleic acid construct upstream of a transgene to drive expression of the transgene.

In an embodiment, the method 1900 may comprise producing an adeno associated virus or a lentivirus comprising the nucleic acid construct.

Figure 20:
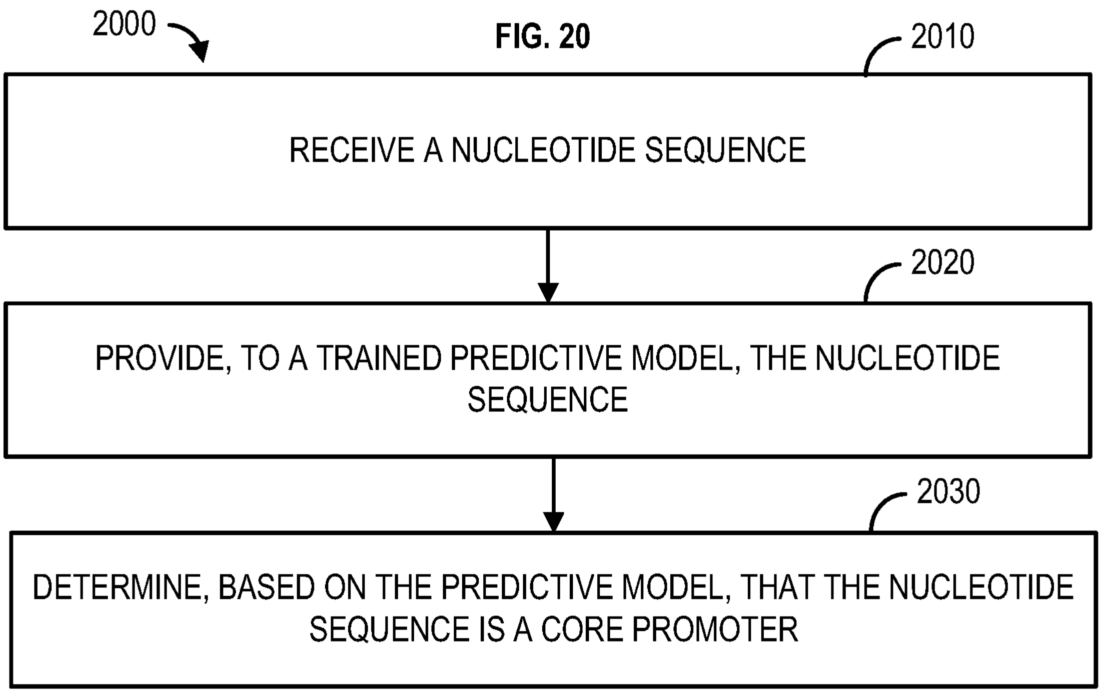
FIG. 20 shows an example method.

In an embodiment, the predictive module 1526 may be configured to perform a method 2000, shown in FIG. 20. The method 2000 may be performed in whole or in part by a single computing device, a plurality of electronic devices, and the like. The method 2000 may comprise receiving a nucleotide sequence at 2010. Receiving the nucleotide sequence may comprise receiving a plurality of nucleotide sequences, wherein the plurality of nucleotide sequences were generated by a generative model.

The method 2000 may comprise providing, to a trained predictive model, the nucleotide sequence at 2020.

The method 2000 may comprise determining, based on the predictive model, that the nucleotide sequence is a core promoter at 2030.

In an embodiment, the method 2000 may comprise filtering, based on the determination that the nucleotide sequence is a core promoter, the nucleotide sequence according to one or more criteria. The one or more criteria may comprise, for example, one or more of GC content or motif.

In an embodiment, the method 2000 may comprise: receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the associated expression scores satisfying a threshold, a plurality of TSSs from the first plurality of nucleotide sequences, determining, based on the plurality of TSSs, a plurality of summit nucleotide bases, determining, for each summit nucleotide base of the plurality of summit nucleotide bases, an associated plurality of surrounding bases, storing each summit nucleotide base and the associated plurality of surrounding bases as a second plurality of nucleotide sequences labeled as core promoters, determining, for each nucleotide sequence of the second plurality of nucleotide sequences, an associated plurality of shifted bases, storing each associated plurality of shifted bases as a third plurality of nucleotide sequences labeled as not core promoters, generating, based on the second plurality of nucleotide sequences labeled as core promoters and the third plurality of nucleotide sequences labeled as not core promoters, a training data set, determining, based on the training data set, a plurality of features for a predictive model, training, based on a first portion of the training data set, the predictive model according to the plurality of features, testing, based on a second portion of the training data set, the predictive model, and outputting, based on the testing, the predictive model.

Figure 21:
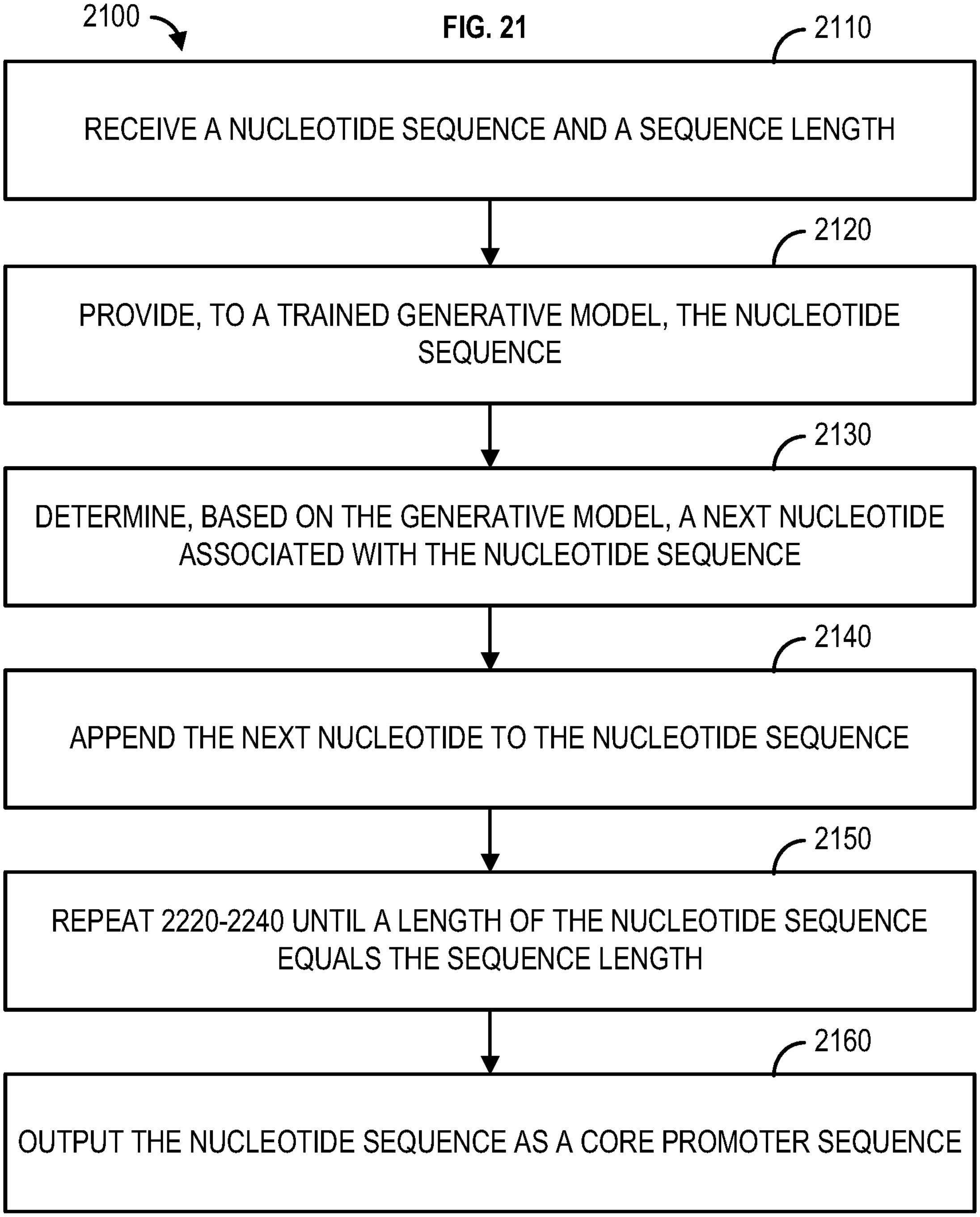
FIG. 21 shows an example method.

In an embodiment, the generative module 1524 may be configured to perform a method 2100, shown in FIG. 21. The method 2100 may be performed in whole or in part by a single computing device, a plurality of electronic devices, and the like. The method 2100 may comprise receiving a nucleotide sequence and a sequence length at 2110.

The method 2100 may comprise providing, to a trained generative model, the nucleotide sequence at 2120.

The method 2100 may comprise determining, based on the generative model, a next nucleotide associated with the nucleotide sequence at 2130.

The method 2100 may comprise appending the next nucleotide to the nucleotide sequence at 2140.

The method 2100 may comprise repeating steps 2120-2140 until a length of the nucleotide sequence equals the sequence length at 2150. The sequence length may be, for example, from about 50 nucleotides to about 100 nucleotides.

The method 2100 may comprise outputting the nucleotide sequence as a core promoter sequence at 2160.

In an embodiment, the method 2100 may comprise engineering a promoter based on the core promoter sequence.

In an embodiment, the method 2100 may comprise inserting the promoter into a nucleic acid construct. Inserting the promoter into the nucleic acid construct may comprise inserting the promoter into the nucleic acid construct upstream of a transgene to drive expression of the transgene.

In an embodiment, the method 2100 may comprise producing an adeno associated virus or a lenti-virus comprising the nucleic acid construct.

In an embodiment, the method 2100 may comprise receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the associated expression scores satisfying a threshold, a third plurality of nucleotide sequences from the second plurality of nucleotide sequences, determining, based on the third plurality of nucleotide sequences, a fourth plurality of nucleotide sequences labeled as not core promoters, generating, based on the third plurality of nucleotide sequences labeled as core promoters and the fourth plurality of nucleotide sequences labeled as not core promoters, a training data set, and training, based on the training data set, a generative model.

In an embodiment, the method 2100 may comprise filtering the nucleotide sequence according to one or more criteria. The one or more criteria may comprise one or more of GC content or motif.

In view of the described methods, systems, and apparatuses and variations thereof, herein below are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising: receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the associated expression scores satisfying a threshold, a plurality of TSSs from the first plurality of nucleotide sequences, determining, based on the plurality of TSSs, a plurality of summit nucleotide bases, determining, for each summit nucleotide base of the plurality of summit nucleotide bases, an associated plurality of surrounding bases, storing each summit nucleotide base and the associated plurality of surrounding bases as a second plurality of nucleotide sequences labeled as core promoters, determining, for each nucleotide sequence of the second plurality of nucleotide sequences, an associated plurality of shifted bases, storing each associated plurality of shifted bases as a third plurality of nucleotide sequences labeled as not core promoters, generating, based on the second plurality of nucleotide sequences labeled as core promoters and the third plurality of nucleotide sequences labeled as not core promoters, a training data set, determining, based on the training data set, a plurality of features for a predictive model, training, based on a first portion of the training data set, the predictive model according to the plurality of features, testing, based on a second portion of the training data set, the predictive model, and outputting, based on the testing, the predictive model.

Embodiment 2: The embodiment as in any one of the preceding embodiments, wherein the associated expression score comprises a Cap Analysis of Gene Expression (CAGE) peak.

Embodiment 3: The embodiment as in any one of the preceding embodiments, wherein determining, based on the plurality of TSSs, the plurality of summit nucleotide bases comprises determining, for each of the plurality of TSSs, a nucleotide base having a strongest CAGE signal.

Embodiment 4: The embodiment as in any one of the preceding embodiments, wherein determining, for each summit nucleotide base of the plurality of summit nucleotide bases, the associated plurality of surrounding bases comprises determining, for each summit nucleotide base of the plurality of summit nucleotide bases, a first plurality of nucleotide bases in the 5' direction and a second plurality of nucleotide bases in the 3' direction.

Embodiment 5: The embodiment as in the embodiment 4, wherein the first plurality of nucleotide bases in the 5' direction comprises 49 nucleotide bases and the second plurality of nucleotide bases in the 3' direction comprises 50 nucleotide bases.

Embodiment 6: The embodiment as in any one of the preceding embodiments, wherein determining, for each nucleotide sequence of the second plurality of nucleotide sequences, the associated plurality of shifted bases comprises shifting a quantity of nucleotide bases away from each nucleotide sequence of the second plurality of nucleotide sequences.

Embodiment 7: The embodiment as in any one of the preceding embodiments, wherein the plurality of features for the predictive model comprises one or more of GC content, AT and CG dinucleotide frequency, ATG frequency, core promoter motif occurrences, relative entropy, and relative positioning relative to an associated TSS.

Embodiment 8: The embodiment as in any one of the preceding embodiments, further comprising filtering out any TSS of the plurality of TSSs from the first plurality of nucleotide sequences having an expression score that overlaps with an expression score for a TSS used in a generative model.

Embodiment 9: The embodiment as in any one of the preceding embodiments, further comprising filtering out any nucleotide sequence of the second plurality of nucleotide sequences containing Ns in the human genome assembly (hg19).

Embodiment 10: A method comprising: receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the second plurality of nucleotide sequences, a third plurality of nucleotide sequences labeled as not core promoters, generating, based on the second plurality of nucleotide sequences labeled as core promoters and the third plurality of nucleotide sequences labeled as not core promoters, a training data set, determining, based on the training data set, a plurality of features for a predictive model, training, based on a first portion of the training data set, the predictive model according to the plurality of features, testing, based on a second portion of the training data set, the predictive model, and outputting, based on the testing, the predictive model.

Embodiment 11: The embodiment as in the embodiment 10, wherein determining, based on the second plurality of nucleotide sequences, a third plurality of nucleotide sequences labeled as not core promoters comprises: determining, for each nucleotide sequence of the second plurality of nucleotide sequences, an associated plurality of shifted bases, and storing each associated plurality of shifted bases as a third plurality of nucleotide sequences labeled as not core promoters.

Embodiment 12: The embodiment as in the embodiments 11, wherein determining, for each nucleotide sequence of the second plurality of nucleotide sequences, the associated plurality of shifted bases comprises shifting a quantity of nucleotide bases away from each nucleotide sequence of the second plurality of nucleotide sequences.

Embodiment 13: The embodiment as in any of the embodiments 10-12, wherein the associated expression score comprises a Cap Analysis of Gene Expression (CAGE) peak.

Embodiment 14: The embodiment as in any of the embodiments 10-13, wherein determining, based on the first plurality of nucleotide sequences, the second plurality of nucleotide sequences labeled as core promoters comprises: determining, based on the associated expression scores satisfying a threshold, a plurality of TSSs from the first plurality of nucleotide sequences, determining, based on the plurality of TSSs, a plurality of summit nucleotide bases, determining, for each summit nucleotide base of the plurality of summit nucleotide bases, an associated plurality of surrounding bases, and storing each summit nucleotide base and the associated plurality of surrounding bases as the second plurality of nucleotide sequences labeled as core promoters.

Embodiment 15: The embodiment as in the embodiment 14, wherein determining, based on the plurality of TSSs, the plurality of summit nucleotide bases comprises determining, for each of the plurality of TSSs, a nucleotide base having a strongest CAGE signal.

Embodiment 16: The embodiment as in the embodiment 14, wherein determining, for each summit nucleotide base of the plurality of summit nucleotide bases, the associated plurality of surrounding bases comprises determining, for each summit nucleotide base of the plurality of summit nucleotide bases, a first plurality of nucleotide bases in the 5' direction and a second plurality of nucleotide bases in the 3' direction.

Embodiment 17: The embodiment as in the embodiment 16, wherein the first plurality of nucleotide bases in the 5' direction comprises 49 nucleotide bases and the second plurality of nucleotide bases in the 3' direction comprises 50 nucleotide bases.

Embodiment 18: The embodiment as in any of the embodiments 10-17, wherein the plurality of features for the predictive model comprises one or more of GC content, AT and CG dinucleotide frequency, ATG frequency, core promoter motif occurrences, relative entropy, and relative positioning relative to an associated TSS.

Embodiment 19: The embodiment as in any of the embodiments 14-18, further comprising filtering out any TSS of the plurality of TSSs from the first plurality of nucleotide sequences having an expression score that overlaps with an expression score for a TSS used in a generative model.

Embodiment 20: The embodiment as in any of the embodiments 10-19, further comprising filtering out any nucleotide sequence of the second plurality of nucleotide sequences containing Ns in the human genome assembly (hg19).

Embodiment 21: A method comprising: receiving genetic data, wherein the genetic data comprises a first plurality of nucleotide sequences, wherein each nucleotide sequence of the plurality of nucleotide sequences comprises at least one transcription start site (TSS) having an associated expression score, normalizing the genetic data, clustering, based on the associated expression scores, the TSSs, determining, for each cluster of TSSs, an interquantile width, labeling, based on the interquantile width, each TSS as a sharp TSS or a broad TSS, determining, based on the plurality of TSSs, a plurality of summit nucleotide bases, determining, for each summit nucleotide base of the plurality of summit nucleotide bases, an associated plurality of surrounding bases, storing each summit nucleotide base and the associated plurality of surrounding bases as a second plurality of nucleotide sequences labeled as core promoters, determining, based on the associated expression scores satisfying a threshold, a third plurality of nucleotide sequences from the second plurality of nucleotide sequences, determining, for each nucleotide sequence of the third plurality of nucleotide sequences, an associated plurality of shifted bases, storing each associated plurality of shifted bases as a fourth plurality of nucleotide sequences labeled as not core promoters, generating, based on the third plurality of nucleotide sequences labeled as core promoters and the fourth plurality of nucleotide sequences labeled as not core promoters, a training data set, generating, for each nucleotide sequence in the training data set, a plurality of seed sequence and target nucleotide pairs, vectorizing each seed sequence and target nucleotide pair of the plurality of seed sequence and target nucleotide pairs, training, based on the vectorized seed sequence and target nucleotide pairs, a generative model, and outputting the generative model.

Embodiment 22: The embodiment as in the embodiment 21, wherein the associated expression score comprises a Cap Analysis of Gene Expression (CAGE) peak.

Embodiment 23: The embodiment as in any of the embodiments 21-22, wherein determining, based on the plurality of TSSs, the plurality of summit nucleotide bases comprises determining, for each of the plurality of TSSs, a nucleotide base having a strongest CAGE signal.

Embodiment 24: The embodiment as in any of the embodiments 21-23, wherein determining, for each summit nucleotide base of the plurality of summit nucleotide bases, the associated plurality of surrounding bases comprises determining, for each summit nucleotide base of the plurality of summit nucleotide bases, a first plurality of nucleotide bases in the 5' direction and a second plurality of nucleotide bases in the 3' direction.

Embodiment 25: The embodiment as in the embodiment 24, wherein the first plurality of nucleotide bases in the 5' direction comprises 49 nucleotide bases and the second plurality of nucleotide bases in the 3' direction comprises 50 nucleotide bases.

Embodiment 26: The embodiment as in any of the embodiments 21-25, wherein determining, for each nucleotide sequence of the third plurality of nucleotide sequences, the associated plurality of shifted bases comprises shifting a quantity of nucleotide bases away from each nucleotide sequence of the third plurality of nucleotide sequences.

Embodiment 27: The embodiment as in any of the embodiments 21-26, further comprising filtering out any nucleotide sequence of the second plurality of nucleotide sequences containing Ns in the human genome assembly (hg19).

Embodiment 28: The embodiment as in any of the embodiments 21-27, wherein each seed sequence and target nucleotide pair comprises a seed sequence having a defined length and a target nucleotide immediately following the seed sequence on a given nucleotide sequence.

Embodiment 29: The as in the embodiment 28, wherein the defined length is 10 bases.

Embodiment 30: The embodiment as in any of the embodiments 21-29, wherein generating, for each nucleotide sequence in the training data set, the plurality of seed sequence and target nucleotide pairs comprises: dividing, based on sharp TSS or broad TSS labeling, the nucleotide sequences in the training data set into a sharp TSS group or a broad TSS group, applying a sliding window of the defined length and having a defined step size to each nucleotide sequence, and storing, at each step of the sliding window, a seed sequence and target nucleotide pair.

Embodiment 31: The embodiment as in any of the embodiments 21-30, wherein vectorizing each seed sequence and target nucleotide pair of the plurality of seed sequence and target nucleotide pairs comprises encoding each nucleotide as a respective number.

Embodiment 32: The embodiment as in any of the embodiments 21-31, wherein the generative model comprises a long-short term memory (LSTM) recurrent neural network (RNN).

Embodiment 33: The embodiment as in any of the embodiments 21-32, further comprising generating, based on the generative model, a nucleotide sequence.

Embodiment 34: The embodiment as in the embodiment 33, wherein generating, based on the generative model, the nucleotide sequence comprises: (a) receiving a seed sequence, (b) predicting, based on the seed sequence, a next nucleotide, (c) appending the next nucleotide to the seed sequence, and (d) repeating b-c until a desired length for the nucleotide sequence is reached.

Embodiment 35: The as in the embodiment 34, wherein the desired length is from about 50 nucleotides to about 100 nucleotides.

Embodiment 36: The embodiment as in any of the embodiments 33-35, wherein the nucleotide sequence is a core promoter sequence.

Embodiment 37: The as in the embodiment 36, further comprising engineering a promoter based on the core promoter sequence.

Embodiment 38: The as in the embodiment 37, further comprising inserting the promoter into a nucleic acid construct.

Embodiment 39: The as in the embodiment 38, wherein inserting the promoter into the nucleic acid construct comprises inserting the promoter into the nucleic acid construct upstream of a transgene to drive expression of the transgene.

Embodiment 40: The as in any of the embodiments 38-39, further comprising producing an adeno associated virus or a lentivirus comprising the nucleic acid construct.

Embodiment 41: A method comprising: receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the associated expression scores satisfying a threshold, a third plurality of nucleotide sequences from the second plurality of nucleotide sequences, determining, based on the third plurality of nucleotide sequences, a fourth plurality of nucleotide sequences labeled as not core promoters, generating, based on the third plurality of nucleotide sequences labeled as core promoters and the fourth plurality of nucleotide sequences labeled as not core promoters, a training data set, training, based on the training data set, a generative model, and outputting the generative model.

Embodiment 42: The as in the embodiment 41, further comprising normalizing the genetic data.

Embodiment 43: The embodiment as in any of the embodiments 41-42, further comprising: clustering, based on the associated expression scores, the TSSs, determining, for each cluster of TSSs, an interquantile width, and labeling, based on the interquantile width, each TSS as a sharp TSS or a broad TSS.

Embodiment 44: The embodiment as in any of the embodiments 41-43, wherein determining, based on the third plurality of nucleotide sequences, the fourth plurality of nucleotide sequences labeled as not core promoters comprises: determining, for each nucleotide sequence of the third plurality of nucleotide sequences, an associated plurality of shifted bases, and storing each associated plurality of shifted bases as a fourth plurality of nucleotide sequences labeled as not core promoters.

Embodiment 45: The embodiment as in any of the embodiments 41-44, wherein training, based on the training data set, the generative model comprises: generating, for each nucleotide sequence in the training data set, a plurality of seed sequence and target nucleotide pairs, vectorizing each seed sequence and target nucleotide pair of the plurality of seed sequence and target nucleotide pairs, and training, based on the vectorized seed sequence and target nucleotide pairs, the generative model.

Embodiment 46: The embodiment as in any of the embodiments 41-45, wherein the associated expression score comprises a Cap Analysis of Gene Expression (CAGE) peak.

Embodiment 47: The embodiment as in any of the embodiments 41-46, wherein determining, based on the first plurality of nucleotide sequences, the second plurality of nucleotide sequences labeled as core promoters comprises: determining, based on the plurality of TSSs, a plurality of summit nucleotide bases, determining, for each summit nucleotide base of the plurality of summit nucleotide bases, an associated plurality of surrounding bases, and storing each summit nucleotide base and the associated plurality of surrounding bases as the second plurality of nucleotide sequences labeled as core promoters.

Embodiment 48: The embodiment as in the embodiment 47, wherein determining, based on the plurality of TSSs, the plurality of summit nucleotide bases comprises determining, for each of the plurality of TSSs, a nucleotide base having a strongest CAGE signal.

Embodiment 49: The embodiment as in any of the embodiments 47-48, wherein determining, for each summit nucleotide base of the plurality of summit nucleotide bases, the associated plurality of surrounding bases comprises determining, for each summit nucleotide base of the plurality of summit nucleotide bases, a first plurality of nucleotide bases in the 5' direction and a second plurality of nucleotide bases in the 3' direction.

Embodiment 50: The embodiment as in the embodiment 49, wherein the first plurality of nucleotide bases in the 5' direction comprises 49 nucleotide bases and the second plurality of nucleotide bases in the 3' direction comprises 50 nucleotide bases.

Embodiment 51: The embodiment as in any of the embodiments 41-50, wherein determining, for each nucleotide sequence of the third plurality of nucleotide sequences, the associated plurality of shifted bases comprises shifting a quantity of nucleotide bases away from each nucleotide sequence of the third plurality of nucleotide sequences.

Embodiment 52: The embodiment as in any of the embodiments 41-51, further comprising filtering out any nucleotide sequence of the second plurality of nucleotide sequences containing Ns in the human genome assembly (hg19).

Embodiment 53: The embodiment as in any of the embodiments 45-52, wherein each seed sequence and target nucleotide pair comprises a seed sequence having a defined length and a target nucleotide immediately following the seed sequence on a given nucleotide sequence.

Embodiment 54: The embodiment as in the embodiment 53, wherein the defined length is 10 bases.

Embodiment 55: The embodiment as in any of the embodiments 45-54, wherein generating, for each nucleotide sequence in the training data set, the plurality of seed sequence and target nucleotide pairs comprises: dividing, based on sharp TSS or broad TSS labeling, the nucleotide sequences in the training data set into a sharp TSS group or a broad TSS group, applying a sliding window of the defined length and having a defined step size to each nucleotide sequence, and storing, at each step of the sliding window, a seed sequence and target nucleotide pair.

Embodiment 56: The embodiment as in any of the embodiments 45-55, wherein vectorizing each seed sequence and target nucleotide pair of the plurality of seed sequence and target nucleotide pairs comprises encoding each nucleotide as a respective number.

Embodiment 57: The embodiment as in any of the embodiments 41-56, wherein the generative model comprises a long-short term memory (LSTM) recurrent neural network (RNN).

Embodiment 58: The embodiment as in any of the embodiments 41-57, further comprising generating, based on the generative model, a nucleotide sequence.

Embodiment 59: The embodiment as in the embodiment 58, wherein generating, based on the generative model, the nucleotide sequence comprises: (a) receiving a seed sequence, (b) predicting, based on the seed sequence, a next nucleotide, (c) appending the next nucleotide to the seed sequence, and d) repeating b-c until a desired length for the nucleotide sequence is reached.

Embodiment 60: The embodiment as in the embodiment 59, wherein the desired length is from about 50 nucleotides to about 100 nucleotides.

Embodiment 61: The embodiment as in any of the embodiments 41-61, wherein the nucleotide sequence is a core promoter sequence.

Embodiment 62: The embodiment as in the embodiment 61, further comprising engineering a promoter based on the core promoter sequence.

Embodiment 63: The embodiment as in the embodiment 62, further comprising inserting the promoter into a nucleic acid construct.

Embodiment 64: The embodiment as in the embodiment 63, wherein inserting the promoter into the nucleic acid construct comprises inserting the promoter into the nucleic acid construct upstream of a transgene to drive expression of the transgene.

Embodiment 65: The embodiment as in the embodiment 64, further comprising producing an adeno associated virus or a lenti-virus comprising the nucleic acid construct.

Embodiment 66: A method comprising: receiving a nucleotide sequence, providing, to a trained predictive model, the nucleotide sequence, and determining, based on the predictive model, that the nucleotide sequence is a core promoter.

Embodiment 67: The embodiment as in the embodiment 66, wherein receiving the nucleotide sequence comprises, receiving a plurality of nucleotide sequences, wherein the plurality of nucleotide sequences were generated by a generative model.

Embodiment 68: The embodiment as in any of the embodiments 66-67, further comprising filtering, based on the determination that the nucleotide sequence is a core promoter, the nucleotide sequence according to one or more criteria.

Embodiment 69: The embodiment as in the embodiment 68, wherein the one or more criteria comprise one or more of GC content or motif.

Embodiment 70: The embodiment as in any of the embodiments 66-69, further comprising: receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the associated expression scores satisfying a threshold, a plurality of TSSs from the first plurality of nucleotide sequences, determining, based on the plurality of TSSs, a plurality of summit nucleotide bases, determining, for each summit nucleotide base of the plurality of summit nucleotide bases, an associated plurality of surrounding bases, storing each summit nucleotide base and the associated plurality of surrounding bases as a second plurality of nucleotide sequences labeled as core promoters, determining, for each nucleotide sequence of the second plurality of nucleotide sequences, an associated plurality of shifted bases, storing each associated plurality of shifted bases as a third plurality of nucleotide sequences labeled as not core promoters, generating, based on the second plurality of nucleotide sequences labeled as core promoters and the third plurality of nucleotide sequences labeled as not core promoters, a training data set, determining, based on the training data set, a plurality of features for a predictive model, training, based on a first portion of the training data set, the predictive model according to the plurality of features, testing, based on a second portion of the training data set, the predictive model, and outputting, based on the testing, the predictive model.

Embodiment 71: A method comprising: (a) receiving a nucleotide sequence and a sequence length, (b) providing, to a trained generative model, the nucleotide sequence, (c) determining, based on the generative model, a next nucleotide associated with the nucleotide sequence, (d) appending the next nucleotide to the nucleotide sequence, (e) repeating b-d until a length of the nucleotide sequence equals the sequence length, and (f) outputting the nucleotide sequence as a core promoter sequence.

Embodiment 72: The embodiment as in the embodiment 71, further comprising engineering a promoter based on the core promoter sequence.

Embodiment 73: The embodiment as in any of the embodiments 71-72, further comprising inserting the promoter into a nucleic acid construct.

Embodiment 74: The embodiment as in the embodiment 73, wherein inserting the promoter into the nucleic acid construct comprises inserting the promoter into the nucleic acid construct upstream of a transgene to drive expression of the transgene.

Embodiment 75: The embodiment as in any of the embodiments 73-74, further comprising producing an adeno associated virus or a lenti-virus comprising the nucleic acid construct.

Embodiment 76: The embodiment as in any of the embodiments 71-75, wherein the sequence length is from about 50 nucleotides to about 100 nucleotides.

Embodiment 77: The embodiment as in any of the embodiments 71-76, further comprising: receiving genetic data, wherein the genetic data comprises a first plurality of nucleotide sequences, wherein each nucleotide sequence of the plurality of nucleotide sequences comprises at least one transcription start site (TSS) having an associated expression score, determining, based on the first plurality of nucleotide sequences, a second plurality of nucleotide sequences labeled as core promoters, determining, based on the associated expression scores satisfying a threshold, a third plurality of nucleotide sequences from the second plurality of nucleotide sequences, determining, based on the third plurality of nucleotide sequences, a fourth plurality of nucleotide sequences labeled as not core promoters, generating, based on the third plurality of nucleotide sequences labeled as core promoters and the fourth plurality of nucleotide sequences labeled as not core promoters, a training data set, and training, based on the training data set, a generative model.

Embodiment 78: The embodiment as in any of the embodiments 71-77, further comprising filtering the nucleotide sequence according to one or more criteria.

Embodiment 79: The embodiment as in the embodiment 78, wherein the one or more criteria comprise one or more of GC content or motif.

Embodiment 80: An apparatus configured to perform any of the embodiments 1-79.

Embodiment 81: A computer readable medium having processor-executable instructions embodiment thereon configured to cause an apparatus to perform any of the embodiments 1-79.

Those skilled in the art will recognize, or be able to ascertain using no more than routine experimentation, many equivalents to the specific embodiments of the method and compositions described herein. Such equivalents are intended to be encompassed by the following claims.

We claim:

1. A method comprising:

receiving genetic data, wherein the genetic data comprises a first plurality of nucleotide sequences, wherein each nucleotide sequence of the first plurality of nucleotide sequences comprises at least one transcription start site (TSS) having an associated expression score;

determining, based on the first plurality of nucleotide sequences, a second plurality of nucleotide sequences labeled as core promoters;

determining, based on the associated expression scores satisfying a threshold, a third plurality of nucleotide sequences from the second plurality of nucleotide sequences;

determining, based on the third plurality of nucleotide sequences, a fourth plurality of nucleotide sequences labeled as not core promoters;

generating, based on the third plurality of nucleotide sequences labeled as core promoters and the fourth plurality of nucleotide sequences labeled as not core promoters, a training data set;

for each nucleotide sequence in the training data set, vectorizing a plurality of seed sequence and target nucleotide pairs to generate a vectorized training data set;

training, based on the vectorized training data set, a generative model configured to generate a promoter sequence; and outputting the generative model.

2. The method of claim 1, wherein determining, based on the first plurality of nucleotide sequences, the second plurality of nucleotide sequences labeled as core promoters comprises:

determining, based on the plurality of TSSs, a plurality of summit nucleotide bases;

determining, for each summit nucleotide base of the plurality of summit nucleotide bases, an associated plurality of surrounding bases; and storing each summit nucleotide base and the associated plurality of surrounding bases as the second plurality of nucleotide sequences labeled as core promoters.

3. The method of claim 2, wherein determining, based on the plurality of TSSs, the plurality of summit nucleotide bases comprises determining, for each of the plurality of TSSs, a nucleotide base having a strongest Cap Analysis of Gene Expression (CAGE) signal.

4. The method of claim 2, wherein determining, for each summit nucleotide base of the plurality of summit nucleotide bases, the associated plurality of surrounding bases comprises determining, for each summit nucleotide base of the plurality of summit nucleotide bases, a first plurality of nucleotide bases in the 5' direction and a second plurality of nucleotide bases in the 3' direction.

5. The method of claim 4, wherein the first plurality of nucleotide bases in the 5' direction comprises 49 nucleotide bases and the second plurality of nucleotide bases in the 3' direction comprises 50 nucleotide bases.

6. The method of claim 1, wherein determining, based on the third plurality of nucleotide sequences, the fourth plurality of nucleotide sequences labeled as not core promoters comprises:

determining, for each nucleotide sequence of the third plurality of nucleotide sequences, an associated plurality of shifted bases; and storing each of the associated plurality of shifted bases as the fourth plurality of nucleotide sequences labeled as not core promoters.

7. The method of claim 6, wherein determining, for each nucleotide sequence of the third plurality of nucleotide sequences, the associated plurality of shifted bases comprises shifting a quantity of nucleotide bases away from each nucleotide sequence of the third plurality of nucleotide sequences.

8. The method of claim 1, wherein training, based on the vectorized training data set, the generative model comprises:

generating, for each nucleotide sequence in the training data set, the plurality of seed sequence and target nucleotide pairs;

vectorizing each seed sequence and target nucleotide pair of the plurality of seed sequence and target nucleotide pairs; and training, based on the vectorized seed sequence and target nucleotide pairs, the generative model.

9. The method of claim 8, wherein each seed sequence and target nucleotide pair comprises a seed sequence having a defined length and a target nucleotide immediately following the seed sequence on a given nucleotide sequence.

10. The method of claim 8, wherein generating, for each nucleotide sequence in the training data set, the plurality of seed sequence and target nucleotide pairs comprises:

clustering, based on the associated expression scores, the TSSs;

determining, for each cluster of TSSs, an interquantile width;

labeling, based on the interquantile width, each TSS as a sharp TSS or a broad TSS;

dividing, based on sharp TSS or broad TSS labeling, the nucleotide sequences in the training data set into a sharp TSS group or a broad TSS group;

applying a sliding window of the defined length and having a defined step size to each nucleotide sequence; and storing, at each step of the sliding window, a seed sequence and target nucleotide pair.

11. The method of claim 8, wherein vectorizing each seed sequence and target nucleotide pair of the plurality of seed sequence and target nucleotide pairs comprises encoding each nucleotide as a respective number.

12. The method of claim 1, wherein the generative model comprises a long-short term memory (LSTM) recurrent neural network (RNN).

13. The method of claim 1, further comprising generating, based on the generative model, a nucleotide sequence.

14. The method of claim 13, wherein generating, based on the generative model, the nucleotide sequence comprises:

a) receiving a seed sequence;

b) predicting, based on the seed sequence, a next nucleotide;

c) appending the next nucleotide to the seed sequence; and d) repeating b-c until a desired length for the nucleotide sequence is reached, and wherein the nucleotide sequence is a core promoter sequence.

15. The method of claim 14, wherein the desired length is from about 50 nucleotides to about 100 nucleotides.

16. The method of claim 14, further comprising engineering a promoter based on the core promoter sequence.

17. The method of claim 16, further comprising inserting the promoter into a nucleic acid construct.

18. The method of claim 17, wherein inserting the promoter into the nucleic acid construct comprises inserting the promoter into the nucleic acid construct upstream of a transgene to drive expression of the transgene.

19. The method of claim 17, further comprising producing an adeno associated virus or a lenti-virus comprising the nucleic acid construct.

20. The method of claim 14, further comprising:

providing, to a predictive model, the nucleotide sequence; and determining, based on the predictive model, that the nucleotide sequence is a core promoter.

* * * * *

SEQUENCE LISTING

```
Sequence total quantity: 12
SEQ ID NO: 1            moltype = DNA  length = 10
FEATURE                 Location/Qualifiers
misc_feature            1..10
                        note = synthetic construct; promoter sequence
source                  1..10
                        mol_type = other DNA
                        organism = synthetic construct
SEQUENCE: 1
acttgctcga                                                           10

SEQ ID NO: 2            moltype = DNA  length = 11
FEATURE                 Location/Qualifiers
misc_feature            1..11
                        note = synthetic construct; promoter sequence
source                  1..11
                        mol_type = other DNA
                        organism = synthetic construct
SEQUENCE: 2
acttgctcga g                                                         11

SEQ ID NO: 3            moltype = DNA  length = 12
FEATURE                 Location/Qualifiers
misc_feature            1..12
                        note = synthetic construct; promoter sequence
source                  1..12
                        mol_type = other DNA
                        organism = synthetic construct
SEQUENCE: 3
acttgctcga gc                                                        12

SEQ ID NO: 4            moltype = DNA  length = 13
FEATURE                 Location/Qualifiers
misc_feature            1..13
                        note = synthetic construct; promoter sequence
source                  1..13
                        mol_type = other DNA
                        organism = synthetic construct
SEQUENCE: 4
acttgctcga gct                                                       13

SEQ ID NO: 5            moltype = DNA  length = 14
FEATURE                 Location/Qualifiers
misc_feature            1..14
                        note = synthetic construct; promoter sequence
source                  1..14
                        mol_type = other DNA
                        organism = synthetic construct
```

-continued

```
SEQUENCE: 5
acttgctcga gctg                                                   14

SEQ ID NO: 6            moltype = DNA  length = 92
FEATURE                 Location/Qualifiers
source                  1..92
                        mol_type = other DNA
                        organism = Homo sapiens
SEQUENCE: 6
cgttgcccct ctggatccac tgcttaaata cggacgagga cagggccctg tctcctcagc  60
ttcaggcacc accactgacc tgggacagtg aa                               92

SEQ ID NO: 7            moltype = DNA  length = 89
FEATURE                 Location/Qualifiers
source                  1..89
                        mol_type = other DNA
                        organism = Homo sapiens
SEQUENCE: 7
ccctagggta cttatataag ggggtggggg cgcgttcgtc ctcagtcgcg atcgaacact  60
cgagccgagc agacgtgcct acggaccgg                                   89

SEQ ID NO: 8            moltype = DNA  length = 100
FEATURE                 Location/Qualifiers
source                  1..100
                        mol_type = other DNA
                        organism = Homo sapiens
SEQUENCE: 8
agctgaaacc aactcttgag caatataaaa gctgctgccc gggacccagc gcagacggcg  60
gcggcggcgg cggcggcggc ggcggcggcg gcgcagcgct                       100

SEQ ID NO: 9            moltype = DNA  length = 50
FEATURE                 Location/Qualifiers
source                  1..50
                        mol_type = other DNA
                        organism = Homo sapiens
SEQUENCE: 9
cgccgtggct ataaaagcac tgcacacccc gccaacccaa accccggcaa             50

SEQ ID NO: 10           moltype = DNA  length = 84
FEATURE                 Location/Qualifiers
source                  1..84
                        mol_type = other DNA
                        organism = Homo sapiens
SEQUENCE: 10
gggaactggt ataaaagggc cggcgctggt tacccagtcc ttggcgcccc ctcgagccga  60
gcagacgtgt ctagtagatc tcac                                        84

SEQ ID NO: 11           moltype = DNA  length = 89
FEATURE                 Location/Qualifiers
source                  1..89
                        mol_type = other DNA
                        organism = Homo sapiens
SEQUENCE: 11
gggaactggt ataaaagggc cggcgctcgt ggcgttaccc agtccttggc gccccctcga  60
gccgagcaga cgtgtctagt agatctcac                                   89

SEQ ID NO: 12           moltype = DNA  length = 100
FEATURE                 Location/Qualifiers
source                  1..100
                        mol_type = other DNA
                        organism = Homo sapiens
SEQUENCE: 12
gtctctccag ttggatcagg tagataactt tttgaaacat tttcttattg ggaagatctg  60
ggttccattc tgctctctgg gattgcaggt gtgagccaca                       100
```